US008703722B2

(12) United States Patent
Coddens et al.

(10) Patent No.: US 8,703,722 B2
(45) Date of Patent: Apr. 22, 2014

(54) INHIBITORS OF F18+ E COLI BINDING

(75) Inventors: Annelies Coddens, Merelbeke (BE); Eric Cox, Merelbeke (BE); Susann Eva Teneberg, Hindas (SE)

(73) Assignee: Universiteit Gent, Gent (BE)

( * ) Notice: Subject to any disclaimer, the term of this patent is extended or adjusted under 35 U.S.C. 154(b) by 147 days.

(21) Appl. No.: 13/122,002

(22) PCT Filed: Sep. 30, 2009

(86) PCT No.: PCT/EP2009/062699
§ 371 (c)(1),
(2), (4) Date: Jun. 15, 2011

(87) PCT Pub. No.: WO2010/037785
PCT Pub. Date: Apr. 8, 2010

(65) Prior Publication Data
US 2011/0306574 A1 Dec. 15, 2011

(30) Foreign Application Priority Data

Oct. 1, 2008 (GB) .................................. 0817908.7

(51) Int. Cl.
| | |
|---|---|
| *A61K 31/702* | (2006.01) |
| *A61K 31/715* | (2006.01) |
| *A61K 47/30* | (2006.01) |
| *A61K 47/42* | (2006.01) |
| *A61P 31/04* | (2006.01) |
| *C08B 37/00* | (2006.01) |
| *C07K 1/107* | (2006.01) |
| *C07K 14/765* | (2006.01) |
| *C07H 3/06* | (2006.01) |
| *C07H 15/04* | (2006.01) |

(52) U.S. Cl.
USPC ............... 514/25; 514/3.1; 514/53; 435/7.37; 530/395; 530/402; 530/403; 536/53; 536/123.13

(58) Field of Classification Search
None
See application file for complete search history.

(56) References Cited

U.S. PATENT DOCUMENTS

2007/0275881 A1* 11/2007 Morrow et al. .................... 514/8

FOREIGN PATENT DOCUMENTS

| WO | 01/43751 A1 | 6/2001 |
|---|---|---|
| WO | 03/002127 A1 | 1/2003 |
| WO | 03/027245 A2 | 4/2003 |
| WO | 2004/002495 A1 | 1/2004 |
| WO | 2008/071851 A1 | 6/2008 |
| WO | 2008/087260 A1 | 7/2008 |
| WO | 2010/007213 A1 | 1/2010 |

OTHER PUBLICATIONS

Cozens, C. et al "Anti-adhesion methods as novel therapeutics . . . " Exp. Rev. Anti Infect. Ther. (2012) vol. 10, No. 12, pp. 1457-1468.*
Koh, S. et al "Porcine intestinal epithelial cell lines . . . " Vet. Micriobiol. (2008) vol. 130, pp. 191-197.*
Moonens, K. et al "Structural insight into histo-blood group binding . . . " Mol. Microbiol. (2012) vol. 86, No. 1, pp. 82-95.*
Jansson et al., "The Major Subunit, CfaB, of Colonization oFactor Antigen I from Enterotoxigenic *Escherichia coli* Is a Glycosphingolipid Binding Protein", Infection and Immunity, vol. 74, No. 6, pp. 3488-3497, Jun. 2006.
Ali et al., "Structural studies of the O-antigenic polysaccharides from the enteroaggregative *Escherichia coli* strain 87/D2 and international type strains from *E. coli* O128", Carbohydrate Research 343, pp. 695-702, 2008.
PCT/EP2009/062699 International Preliminary Report on Patentability dated Apr. 14, 2011.
Bertschinger et al., "Adhesive fimbriae produced in vivo by *Escherichia coli* O139:K12(B):H1 associated with enterotoxaemia in pigs", Veterinary Microbiology, 25, pp. 267-281, 1990.
Boren et al., "Attachment of *Helicobacter pylori* to Human Gastric Epithelium Mediated by Blood Group Atigens", Science, vol. 262, Dec. 17, 1993.
Coddens et al., "The age-dependent expression of the F18+ *E. coli* receptor on porcine gut epithelial cells is positively correlated with the presence of histo-blood group antigens", ScienceDirect, Veterinary Microbiology, 122, pp. 332-341, 2007.
Coddens et al., "Recognition of Blood Group ABH Type 1 Determinants by the FedF Adhesin of F18-Fimbriated *Escherichia coli*", J. Biol. Chem. vol. 284, No. 15, pp. 9713-9726, Feb. 10, 2009.
Cox et al., "Comparison of the in vitro adhesion of K88, K99, F41 and P987 positive *Escherichia coli* to intestinal villi of 4- to 5-week-old-pigs", Veterinary Microbiology, 34, pp. 7-18, 1993.
Diswall, "Biochemical studies of carbohydrate blood group antigens, Carbohydrate phenotype in relation to cellular glycosyltransferases", University of Gothenburg, Institute of Clinical Sciences, Department of Surgery, 2009.
Imberechts et al., "Characterization of F107 Fimbriae of *Escherichia coli* 107/86, Which Causes Edema Disease in Pigs, and Nucleotide Sequence of the F107 Major Fimbrial Subunit Gene, fedA", Infection and Immunity, vol. 60, No. 5, pp. 1963-1971, May 1992.
Imberechts et al., "Characterization of F18 fimbrial genes fedE and fedF involved in adhesion and length of enterotoxemic *Escherichia coli* strain 107/86", Microbial Pathogenesis, 21, pp. 183-192, 1996.
Liu et al., "Distribution of H Type 1 and H Type 2 Antigens of ABO Blood Group in Different Cells of Huma Submandibular Gland", Journal of Histochemistry & Cytochemistry 46: 69, 1998.
Mathieu et al., "Transgene Expression of α(1,2)-Fucosyltransferase-I (FUT1) in Tumor Cells Selectively Inhibits Sialyl-Lewis x Expression and Binding to E-Selectin without Affecting Synthesis of Sialyl-Lewis a or Binding to P-Selectin", American Journal of Pathology, vol. 164, No. 2, Feb. 2004.

(Continued)

*Primary Examiner* — Leigh Maier
(74) *Attorney, Agent, or Firm* — Dinsmore & Shohl LLP

(57) ABSTRACT

The present invention relates to blood group A/B/H determinant on Type 1 Core glycosphingolipids chains as recognition point for the FedF protein of F18-fimbriated Enterotoxigenic and verotoxinogenic *Escherichia coli* and the use of compounds comprising such determinants for the treatment of F18+ *E. coli* infections in pigs and in screening methods.

10 Claims, 6 Drawing Sheets

(56) References Cited

OTHER PUBLICATIONS

Ruiz-Palacios, "*Campylobacter jejuni* Binds Intestinal H(O) Antigen (Fuc 1, 2Gal 1, 4GlcNAc), and Fucosyloligosaccharides of Human Milk Inhibit Its Binding and Infection", The Journal of Biological Chemistry, vol. 278, No. 16, pp. 14112-14120, Issue of Apr. 18, 2003.

Snoeck et al., "Inhibition of adhesion of F18+ *Escherichia coli* to piglet intestinal villous enterocytes by monoclonal antibody against blood group H-2 antigen", Veterinary Microbiology 100, pp. 241-246, 2004.

Tiels et al., "The excretion of F18+ *E. coli* is reduced after oral immunisation of pigs with a Fed F and F4 fimbriae conjugate", Vaccine 16, pp. 2154-2163, 2008.

Verdonck et al., "Different kinetic of antibody responses following infection of newly weaned pigs with an F4 enterotoxigenic *Escherichia coli* strain or an F18 verotoxigenic *Escherichia coli* strain", Vaccine 20, pp. 2995-3004, 2002.

* cited by examiner

A.

B.

INHIBITORS OF F18+ *E COLI* BINDING

The present invention relates to blood group A/B/H determinant on Type 1 Core glycosphingolipids chains as recognition point for the FedF protein of F18-fimbriated enterotoxigenic and verotoxinogenic *Escherichia coli* and the use of compounds comprising such determinants for the treatment of F18+ *Escherichia coli* infections in pigs and in screening methods.

BACKGROUND OF THE INVENTION

Enterotoxigenic (ETEC) and verotoxigenic (VTEC) *Escherichia coli* (*E. coli*) are important causes of disease in man and animal.

By adhering to the mucosa, bacteria are prevented from being eradicated by the natural cleaning mechanisms of the host such as intestinal peristaltism and secretion of fluid. Furthermore, by being in close contact with the mucosal surfaces, the bacteria have better access to the available nutrients and the secreted toxins are delivered close to their target tissue. Attachment to host tissues is mediated by adhesins expressed on the surface of the microbial organism. The bacterial adhesins are known to be lectins that combine with complementary carbohydrates on the host cell surfaces. The bacterial adhesins are part of typical polymeric structures that are named fimbriae or pili. Fimbriae are thin, flexible filaments with a diameter of 2 to 4 nm without axial hole, whereas pili are rigid structures with diameter of 7-8 nm with axial hole. Both are composed of major subunits that build up the fimbrial shaft complemented with minor subunits that mediate adhesion or have a structural function. In most cases, the adhesin is a minor subunit.

Typically, adhesins consist of two domains: an N-terminal carbohydrate-specific lectin domain and a C-terminal pilin domain. The crystal structures reveal that the lectin domains of these fimbrial adhesins all have an immunoglobulin-like (Ig-like) fold in common, although they show little to no sequence identity. The C-terminal pilin domain connects the adhesin to the fimbrial shaft and shares the highly conserved and incomplete Ig-like fold of the other fimbrial subunits.

Some of the carbohydrates that are recognized by bacterial adhesins have been successfully determined in the past (e.g. those of type 1 and P pili, F5 fimbriae, F17 fimbriae and S fimbriae), whereas other carbohydrate receptor structures remain unsolved as for F4 fimbriae and F6 fimbriae.

Type 1 pili adhesins demonstrate specificity for mannose, but they have a considerable higher affinity for oligosaccharides such as Man$\alpha$3Man$\beta$4GlcNAc and Man$\alpha$6(Man$\alpha$3)Man$\alpha$6(Man$\alpha$3)Man. The biological receptor for the adhesin of type 1 pili (FimH) in the urinary tract is the glycoprotein uroplakin Ia that is strongly expressed by differentiated uroepithelial cells. In addition, the Tamm-Horsfall glycoprotein that is secreted in human urine is recognized by type 1 pili, providing a first line of defense against urinary tract infections.

P fimbriated *E. coli* causing urinary tract infections have specificity for galabiose (Gal$\alpha$4Gal) present in the globoseries of glycolipids on for instance human erythrocytes and uroepithelial cells. The minimum receptor isotype is called globotriasylceramide (GbO3), which is the galabiose residue linked by a $\beta$-glucose residue to a ceramide group that anchors the receptor in the membrane. Other members of the globoseries, namely GbO4 and GbO5, were also found to be recognized by 3 adhesins expressed by PapG alleles (PapGI, PapGII and PapGIII), each adhesin demonstrating a different specificity for a different receptor isotype. Whereas most bacterial lectins recognize terminal non reducing sugars, the P-fimbriated *E. coli* adhesins also recognize internal sugars.

In addition to P pili, other mannose-resistant adhesins, for instance S fimbriae, have been identified in *E. coli* strains associated with human urinary tract or septic infection. These fimbriae bind to sialyl($\alpha$2,3)galactosides on various glycoproteins of human erythrocytes and kidney epithelium, but not on lipids.

F5 fimbriae adhesins, associated with enterotoxigenic *E. coli* that causes diarrhea in neonatal pigs, calves and lambs, recognize NeuGc$\alpha$2-3Gal$\beta$4GlcNAc. This glycolipid receptor structure was first isolated from equine erythrocytes, but is also detected in mucosal scrapings of piglet and calf intestine, thus functioning as in vivo receptor for F5+ *E. coli*.

Not all carbohydrate receptors of pathogenic *E. coli* strains have been identified in the past. Studies to point out the carbohydrate binding specificity of F4+ *E. coli* have not been conclusive so far. The antigenic variants F4ab, F4ac and F4ad each bind their own carbohydrate structure. The sequence Gal$\alpha$3Gal is recognized by F4ab fimbriae, whereas Gal$\beta$3GalNAc and Gal$\beta$3/4GlcNAc are essential parts of the receptor sites of the F4ac variant.

The receptor molecules for fimbrial lectins are glycoprotein or glycolipid in nature. To investigate the glycoprotein receptors involved in adhesion of various bacteria, gelelectrophoresis and immunoblotting techniques are used, followed by overlay assays. Glycolipid receptors for bacterial adhesion are identified and characterized after separation by thin-layer chromatography.

It is known that the carbohydrates being recognized by type 1 pili and S fimbriae are anchored on proteins, whereas the carbohydrate receptors for P pili and F5 fimbriae are located on lipids. The saccharides of glycolipids are easier to determine since each lipid molecule carries only one saccharide chain, in contrast with glycoproteins that may have several N- or O-linked carbohydrate chains on one molecule.

Expression of receptors for pathogenic bacteria is confined to restricted areas of the body, determining the place where infection may occur. In some cases, receptors are only expressed during a limited period in life.

The sugar specificity of fimbriae sometimes is not solely determined by the adhesin, but can also be modulated by the fimbrial shaft.

Interaction between the adhesin and the receptor can activate signal transduction processes that alter gene expression in both bacterial and host cells.

In newly weaned pigs, F18 fimbriated *E. coli* producing entero- and/or verotoxins induce diarrhea and/or edema disease, counting for substantial economical losses in pig industry.

F18 fimbrial structures are expressed by F18+ *E. coli* strains that mediate adhesion with the intestinal brush border. F18 fimbriae are expressed by the fed (fimbriae associated with edema disease) gene cluster and are typically composed of multiple copies of the major subunit FedA whereas a minor subunits FedF is only present in small amounts. FedF was determined to be the adhesive subunit.

The binding domain of FedF is located at the amino-terminal half of the protein, as found in many other bacterial adhesins. The region essential for binding was mapped between amino acid 60 and 109 and the charged amino acid residues Lys-72, His-88 and His-89 were found to be important for receptor binding. These residues could either be directly involved in interaction with the receptor or could influence the tertiary structure of the binding pocket.

A crucial step in pathogenesis of F18+ *E. coli* is the initial attachment to a specific receptor (F18R) on the porcine intestinal epithelium. Some pigs are found to be resistant to colonization by F18+ *E. coli* due to lack of F18R expression. The F18R status of pigs is genetically determined with the gene controlling expression of the F18R mapped to the halothane linkage group on pig chromosome 6. This locus contained two candidate genes, namely FUT1 and FUT2, encoding α(1,2)fucosyltransferases and expression analysis of both genes in the porcine small intestine revealed that the FUT2 gene was differentially expressed, while the FUT1 gene was expressed in all examined pigs. Sequencing of the FUT1 gene of pigs being either susceptible or resistant to F18+ *E. coli* infections showed a polymorphism (G or A) at nucleotide 307. Presence of the A nucleotide on both alleles (FUT1$^{A/A}$ genotype) led to significantly reduced enzyme activity and corresponds with the F18+ *E. coli* resistant genotype, whereas susceptible pigs had either the heterozygous FUT1$^{G/A}$ or the homozygous FUT1$^{G/G}$ genotype. These findings have led to the development of a PCR-RFLP test to differentiate between F18R positive and F18R negative pigs. This test is described in U.S. Pat. No. 6,596,923 which was published on 22 Jul. 2003.

This DNA-test was shown to correlate well with in vivo susceptibility to F18+ *E. coli* infections and is therefore considered to be valuable in predicting the F18R phenotype. However, although an attractive approach to eliminate F18+ *E. coli* infections, genetic selection for F18+ *E. coli* resistant pigs was not routinely used in Belgian pig farms because of reports of genetic association with the stress susceptibility allele (RYR1$^T$) in the Swiss Landrace. Indeed, the genes encoding the F18R were found to be close to the locus for stress susceptibility on porcine chromosome 6. However, by performing positive selection for F18+ *E. coli* resistance in Swiss pigs, the frequency of the resistant FUT1$^A$ allele could be raised to 0.42, while originally not more than 5 to 10% of this population was resistant.

When investigating the association between FUT1$^A$ and RYR1$^T$ alleles more thoroughly in the Belgian pig population, it was found that they were not associated, revealing new potential for this prevention strategy.

Although creating an F18+ *E. coli* resistant pig population could solve the problem of F18+ *E. coli* infections in pigs in a permanent way, it still needs to be ascertained that no co-selection of unwanted traits, other than stress susceptibility, occurs. In addition, it will take several years, if not decades to establish such a population. So, other receptor-based anti-adhesive therapy against F18+ *E. coli* infections could be a great benefit for pig industry.

Several other approaches have been undertaken to eliminate F18+ *E. coli* infections from pig herds.

Immunization trials were performed to protect pigs against F18+ *E. coli*. However, no protective immune response could be induced although a lot of different immunization strategies were performed. This is in contrast with F4+ *E. coli* infections, where oral immunization with F4 fimbriae could induce a protective mucosal immune response.

Immunization of pigs with weak virulent F18+ *E. coli* strains cannot be taken into practice because these strains still produce enterotoxins. Oral administration of F18 fimbriae, encapsulated in poly(D,L-lactide-co-glycolide) (PLGA) particles cannot induce significant amounts of F18-specific serum antibodies nor a reduced colonization upon F18+ *E. coli* challenge. In a more recent study, only a low F18-specific immune response could be induced after oral and intranasal immunization with high concentrations of purified F18 fimbriae (30 mg and 1 mg, respectively) in the presence of the adjuvant LT(R192G) or CTA1-DD, respectively (Verdonck F, Cox E, van Gog K, Van der Stede Y, Duchateau L, Deprez P, Goddeeris B M, 2002. Vaccine 20:2995-3004). In another study delivery of the F18 fimbrial adhesin FedF to the intestinal mucosa was improved by covalent coupling of MBPFedF to F4 fimbriae (Tiels P., Verdonck F., Coddens A., Goddeeris B., Cox E., 2008. Vaccine, 26, 2154-2163). The coupled product could induce a systemic and local FedF-specific immune response and led to a reduction in excretion upon challenge with F18+ *E. coli*. However, no complete protection was obtained.

Also various methods for passive protection against F18+ *E. coli* infections in pigs were tested in the past.

F18-specific antibodies present in chicken egg yolk after immunization of chickens with F18 fimbriae were administered to pigs. They could reduce the shedding of F18+ *E. coli* and diminished the amount of diarrhea and death after experimental infection of pigs. Verotoxin II-specific antibodies injected intramuscularly one day before weaning could protect pigs from symptoms of edema disease. However, since no reduction in colonization of F18+ *E. coli* is obtained, F18+ *E. coli* strains will still emerge in the environment. Therefore, it is better to interfere with the initial attachment of the bacterium with the host, which is the first step in the infection process.

Colonization of the porcine gut with F18+ *E. coli* could be reduced by oral administration of non-immune plasma powder, derived from blood of healthy slaughter pigs. This protective effect of porcine plasma powder was suggested to be due to glycan moieties present on plasma glycoproteins, although this needs further proof Another approach against F18+ *E. coli* could be replacing some or all of the plant-based proteins supplemented in pig feed by animal-based proteins (U.S. Pat. No. 6,355,859 published on 12 Apr. 2002: Interactions between genotype and diet in swine that prevent *E. coli* associated intestinal disease). Suitable animal-based proteins include milk, blood plasma and fish meal. A drawback of these last methods is that the concentration of the carbohydrates required for effective inhibition of adhesion in vitro or in vivo is high.

Although the biological function of histo-blood group antigens is not clarified yet, it has been reported before that histo-blood group antigens can act as receptors for pathogenic organisms. Several bacteria, including *Helicobacter pylori* and *Campylobacter jejuni*, have been shown to utilise blood group determinants as receptors to facilitate their colonisation. While *C. jejuni* binds to the blood group H type 2 determinant (Ruiz-Palacios G M, Cervantes L E, Ramos P, Chavez-Munguia B, Newburg D S, 2003. J Biol Chem. 278 (16):14112-20), the primary receptor for *H. pylori* is the Le$^b$ determinant (Fucα2Galβ3(Fucα4)GlcNAc), along with a lower affinity binding to the H type 1 determinant (Borén T, Falk P, Roth K A, Larson G, Normark S, 1993. Science. 262(5141):1892-5). Binding to Le$^b$ and the H type 1 determinant is mediated by the BabA adhesion. Recently the adaption of the BabA adhesin to the fucosylated blood group antigens most prevalent in the local population was described. In Europe and the US, where the blood group ABO phenotypes are common in the population, the *H. pylori* strains (designated generalist strains) bind to blood group A, B, and O type 1 determinants However, in populations such as the South American native population, which only have the blood group O phenotype, the *H. pylori* strains (designated specialist strains) bind only to the blood group O determinants (Le$^b$ and the H type 1).

Viral binding to blood group antigens has also been reported. H type 2 histo-blood group trisaccharides on rabbit epithelium are recognized by Rabbit Hemorrhagic Disease Virus (RHDV) and H type 1 and H types 3/4 on gastroduodenal epithelial cells of secretor individuals are used by Norwalk virus as ligands.

The synthesis of histo-blood group antigens requires several glycosyltransferases acting on precursor oligosaccharides, such as type 1 (Galβ3GlcNAcβ-R) and type 2 precursor chains (Galβ4GlcNAcβ-R). These precursors are converted into H antigens by the action of an α(1,2)fucosyltransferase adding a fucose in an α1,2 linkage. In pigs, two genes encoding fucosyltransferases, FUT1 and FUT2, have been identified, but only the polymorphism on base pair 307 of FUT1 was found to be associated with resistance to F18+ *E. coli* infections. Human and porcine FUT1 preferentially fucosylate type 2 precursor chains in vitro pointing to a link between type 2 carbohydrate chains and the F18R. Nevertheless, some studies indicate that FUT1 can be responsible for α1,2 fucosylation of type 1 chains in vitro and in vivo (Liu Y H, Fujitani N, Koda Y, Kimura H, 1998. J Histochem Cytochem. 46:69-76, Mathieu S, Prorok M, Benoliel A M, Uch R, Langlet C, Bongrand P, Gerolami R, El-Battari A, 2004. Am J Pathol. 164:371-383).

A previous study of Snoeck et al. (Veterinary Microbiology 100, (2004) 241-246) describes the inhibition of adhesion of F18+ *E. coli* to piglet intestinal villous enterocytes by monoclonal antibody against blood group H-2 antigens. A publication of Coddens et al. (Veterinary Microbiology 122, (2007) 332-341) reports that the age dependent expression of the F18+ *E. coli* receptor on porcine gut epithelial cells is positively correlated with the presence of H histo-blood group antigens on type 2 core chains.

These previous studies are correlative and suggest that the F18 receptor contains the blood group antigen H-2 in its carbohydrate structure. However, the identity and nature of the F18R molecule remained unclear.

Unexpectedly, the present invention demonstrate that the FedF adhesin of F18 fimbriated *E. coli* recognizes glycosphingolipids (GSLs) with blood group A, B or H determinants on type 1 and type 4 core chains while blood group A, B or H determinants on type 2 core chains are not recognized. Pure A type 3 GSL's were not available for testing.

Thus the problem solved by the present invention is the identification of carbohydrate structures that are recognized by F18+ *E. coli*. Identification of the interaction of the above-mentioned A/B/H blood group determinants on type 1 and type 4 core chains with F18+ *E. coli* can be applied for receptor-based prevention strategies against F18+ *E. coli* infections in pigs. In contrast to antibiotics, administration of specific inhibitors of the interaction between F18+ *E. coli* and the F18 receptor is a gentle and safe way to counteract bacterial infections. Furthermore, since receptor-based prevention strategies do not act by killing or arresting the growth of the infectious agent, it is assumed that strains resistant to such agents will arise to a lesser extent compared to strains resistant to antibiotics. Identification of the carbohydrate structures that are recognized by F18+ *E. coli* makes it possible to supplement pig feed with very specific molecules that interfere with the interaction between F18+ *E. coli* and the gut epithelium at low concentrations when compared with less specific inhibitors such as e.g. blood plasma, or the combination therapies such as for example described in WO2004/002495.

SUMMARY OF THE INVENTION

The present invention is concerned with the use of a compound for binding to F18+ *E. coli*, F18 fimbriae, F18 adhesin, FedF or the receptor binding domain of FedF wherein said compound is a compound of formula (I)

[X(Fucα2)Galβ3(Y)TV]$_n$-W    (I)

wherein
  X is absent, Galα3 or GalNAcα3 and when X is absent, then Y is absent;
  Y is absent or Fucα4;
  T is absent or ZNAcε3;
    and wherein Z is Glc or Gal; and
    ε is α or β;
  V is absent or a mono- or polysaccharide;
  n is 1 or more; and
  W is absent or a carrier capable of binding n (one or more) polysaccharide chains In a further embodiment of the present invention V is UGalβ4Glcβ1; and wherein U is absent, Galα4, Galβ3GlcNAcβ3, or (Fucα2)Galβ3GlcNAcβ3

In a further embodiment, W is a mono- or polysaccharide, a protein, a lipid, a glycolipid, a glycoprotein, a glycosphingolipid or a ceramide.

In a particular embodiment of the present invention X is Galα3 or GalNAcα3; Z is Glc or Gal and Y is absent.

In another particular embodiment of the present invention X, Y, T and V are absent.

In yet a further embodiment ε is β and/or Z is Glc.

As a further embodiment, the present invention provides the use of a compound as described herein wherein said compound is a compound of formula (Ia)

[X(Fucα2)Galβ3(Y)ZNAcε3UGalβ4Glcβ1]$_n$-W    (Ia)

wherein
  U is absent, Galα4, Galβ3GlcNAcβ3, or (Fucα2) Galβ3GlcNAcβ3

Another embodiment of the present invention is to the use of a compound as described herein wherein W is absent or ceramide, and wherein said ceramide is d18:1-16:0, t18:0-16:0, t18:0-h16:0, t18:0-h22:0 or t18:0-h24:0.

Another aspect of the present invention is the use of a compound as described herein, wherein said compound is

[Fucα2Galβ3]$_n$-W;

[Fucα2Galβ3GlcNAcβ3Galβ4Glcβ1]$_n$-W;

[Galα3(Fucα2)Galβ3GlcNAcβ3Galβ4Glcβ1]$_n$-W;

[GalNAcα3(Fucα2)Galβ3GlcNAcβ3Galβ4Glcβ1]$_n$-W;

[GalNAcα3(Fucα2)Galβ3(Fucα4)
  GlcNAcβ3Galβ4Glcβ1]$_n$-W;

[Galα3(Fucα2)Galβ3(Fucα4)GlcNAcβ3Galβ4Glcβ1]$_n$-W;

[GalNAcα3(Fucα2)
  Galβ3GlcNAcβ3Galβ3GlcNAcβ3Galβ4Glcβ1]$_n$-W;

[GalNAcα3(Fucα2)
  Galβ3GalNAcβ3Galα4Galβ4Glcβ1]$_n$-W; or

[GalNAcα3(Fucα2)Galβ3GalNAcα3(Fucα2)
  Galβ3GlcNAcβ3Galβ4Glcβ1]$_n$-W

The invention is also concerned with a compound of formula (I) or (Ia) wherein the compound is

[GalNAcα3(Fucα2)Galβ3GalNAcα3(Fucα2)
  Galβ3GlcNAcβ3Galβ4Glcβ1]$_n$-W

The invention is further concerned with the above described compounds for use as a medicine, for use in the treatment of F18+ *E. coli* infections in pigs in particular in the treatment of post weaning diarrhea and edema disease in pigs or for the manufacture of a medicament for the treatment of F18+ *E. coli* infections in pigs in particular in the treatment of post weaning diarrhea and edema disease in pigs.

The invention is also concerned with screening methods such as the use of a compound as described above in a method to identify molecules that affect the binding between F18+ *E. coli*, F18 fimbriae, F18 adhesin, FedF or the receptor binding domain of FedF and said compound. In particular the invention is concerned with a method to identify molecules that bind to the above described compounds said method comprising:

contacting the molecule to be tested with said compound, and determining whether said molecule binds to said compound.

The invention is also concerned with a method to identify molecules that affect the binding between F18+ *E. coli*, F18 fimbriae, F18 adhesin, FedF or the receptor binding domain of FedF and the compound described above comprising:

contacting the molecule to be tested with F18+ *E. coli*, F18 fimbriae, F18 adhesins, FedF or the receptor binding domain of FedF; and said compound, and determining whether said molecule affects the binding of F18+ *E. coli*, F18 fimbriae, F18 adhesin, FedF or the receptor binding domain of FedF with said compound.

In these methods the F18+ *E. coli*, F18 fimbriae, F18 adhesins, FedF or the receptor binding domain of FedF, the compound as described above and/or the molecule to be tested can be labelled. The compound, the molecule, the F18+ *E. coli*, F18 fimbriae, F18 adhesins, FedF or the receptor binding domain of FedF can be present on a solid support, a cell or a tissue. The method can further comprise:

performing a chromatogram binding assay; or performing the villous adhesion test.

The invention is further related to molecules identified in the above described methods. This molecule can be a lectin, an antibody, a protein, a glycoprotein, a glycolipid, a glycosphingolipid, a small molecule or a synthetic mimic of a compound as described above. Said molecule can be an F18R receptor analogue or a molecule that blocks the F18R receptor.

The invention also provides a pharmaceutical composition comprising pharmaceutically acceptable carriers and as an active ingredient a therapeutically effective amount of a compound as described above. In another embodiment the invention provides a process of preparing such a pharmaceutical composition wherein the pharmaceutically acceptable carriers and a compound as described above are intimately mixed.

A further aspect of the invention is a food or drink additive comprising a compound or a molecule as described above. Another aspect of the invention is pig feed supplemented with a compound, a molecule, a pharmaceutical composition or a food additive as described above.

Finally the present invention also provides the use of a compound, a molecule, a pharmaceutical composition, a food or drink additive or pig feed as described above to differentiate between F18R positive and negative pigs.

(B) Anomeric region of the 600 MHz proton NMR spectrum of fraction A-II (30° C.). The sample was dissolved in dimethyl sulphoxide-D$_2$O (98:2, by volume) after deuterium exchange.

Figure 5:
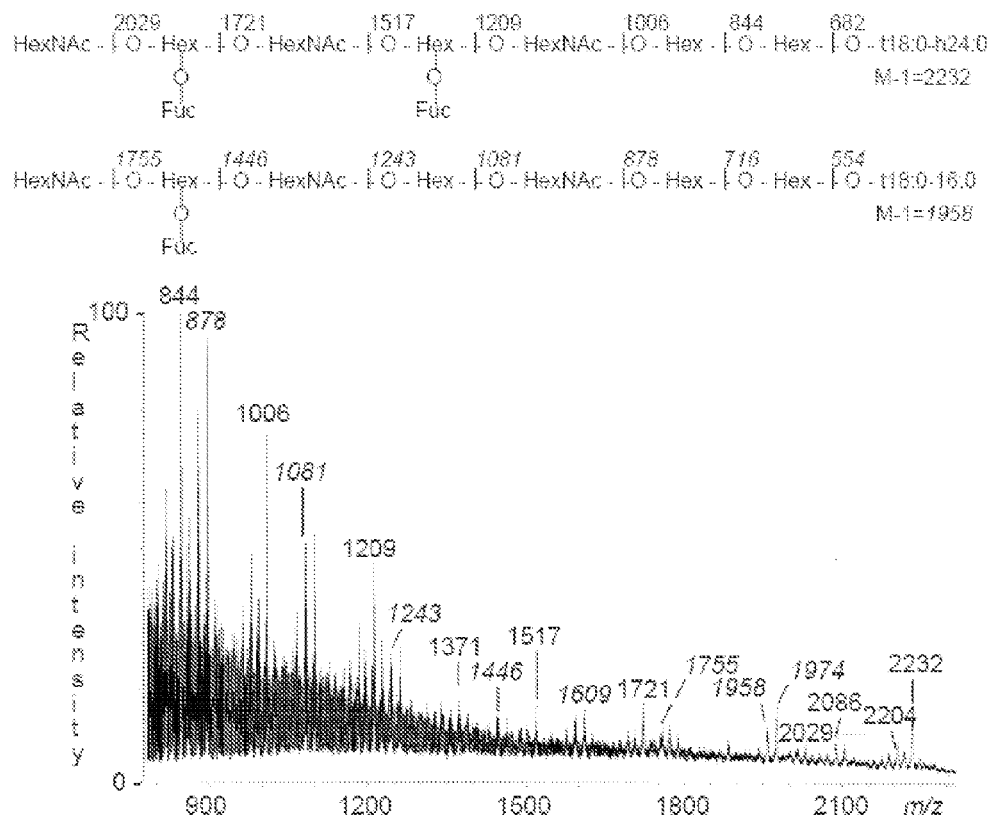

FIG. 5: Negative ion FAB mass spectrum of the F18 fimbriated *E. coli* binding glycosphingolipid fraction A-III, isolated from blood group A pig intestinal epithelium.

Above the spectrum are interpretation formulae representing an octaglycosylceramide with t18:0-16:0 ceramide and a nonaglycosylceramide with t18:0-h24:0 ceramide, respectively. The analysis was done as described in the "Example 7".

Figure 6:
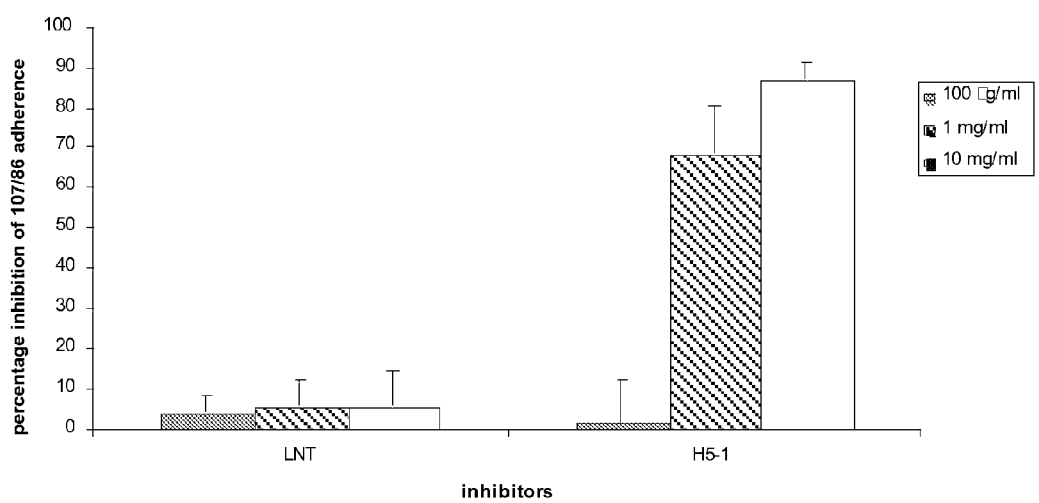

FIG. 6: Effect of pre-incubation of F18-fimbriated *E. coli* with oligosaccharides. 18+ *E. coli* strain 107/86 was incubated with blood group H type 1 pentasaccharide or lacto-N-tetraose saccharide in PBS for 1 h at room temperature. Thereafter, the suspensions were utilized in the in vitro villous adhesion assay.

Figure 7:
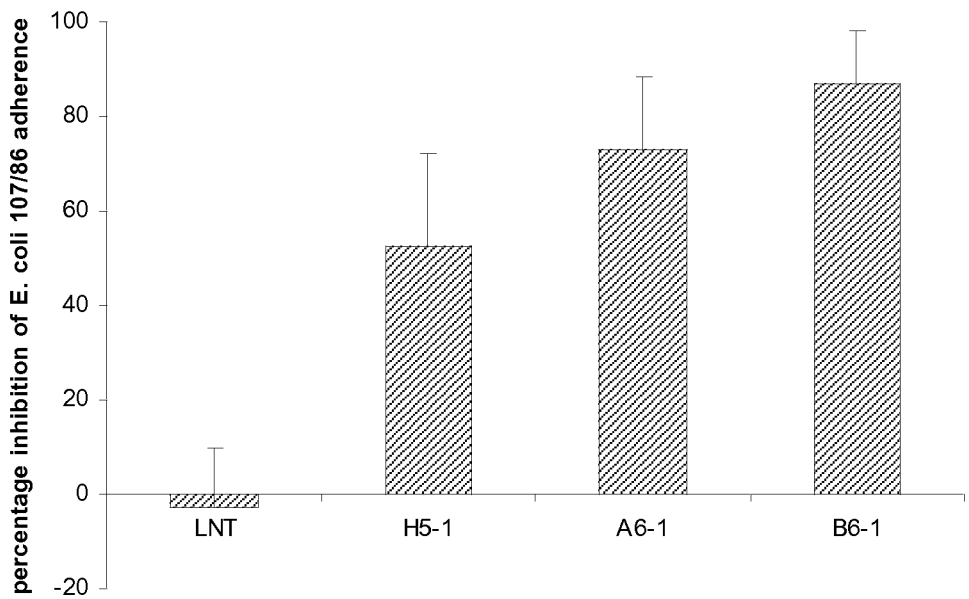

FIG. 7: Effect of pre-incubation of F18+ *E. coli* with oligosaccharides. F18+ *E. coli* strain 107/86 was incubated with blood group H type 1 pentasaccharide (H5-1), blood group A type 1 hexasaccharide (A6-1), blood group B type 1 hexasaccharide (B6-1) or lacto-N-tetraose saccharide (LNT) in PBS for 1 h at room temperature. Thereafter, the suspensions were utilized in the in vitro villous adhesion assay.

Figure 8:
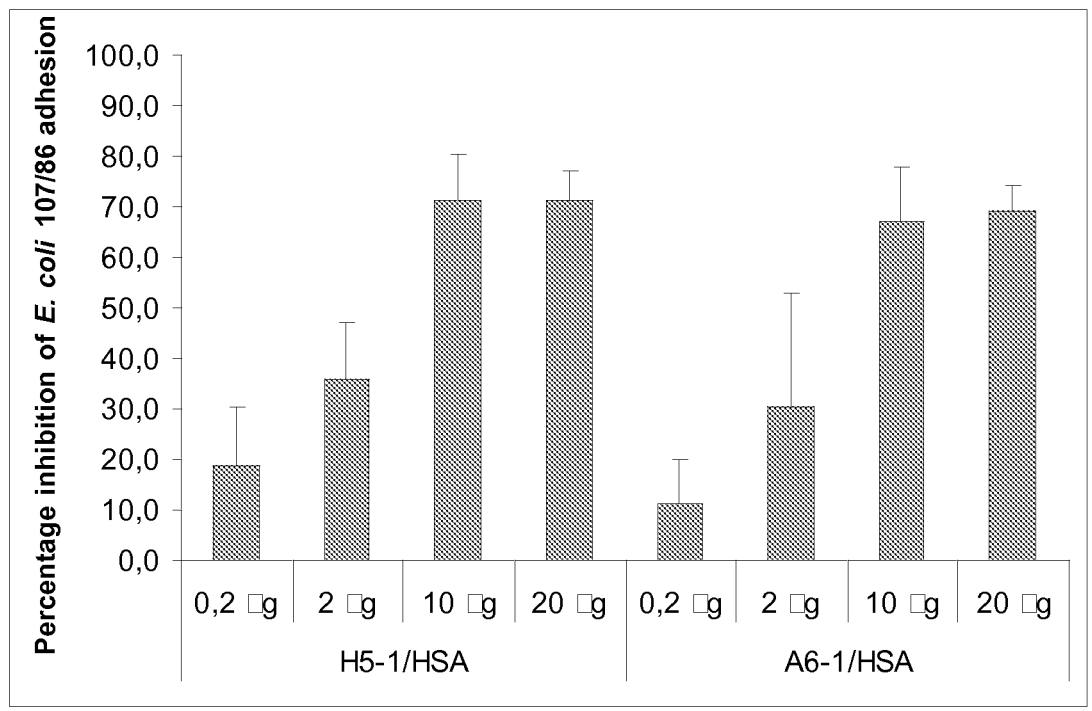

FIG. 8: Effect of pre-incubation of F18+ *E. coli* with multivalent blood group sugars. F18+ *E. coli* strain 107/86 was incubated with different concentrations of blood group H type 1 pentasaccharide conjugated to HSA (H5-1/HSA) or blood group A type 1 hexasaccharide conjugated to HSA (A6-1/HSA) in PBS for 1 h at room temperature. Thereafter, the suspensions were utilized in the in vitro villous adhesion assay.

Figure 9:
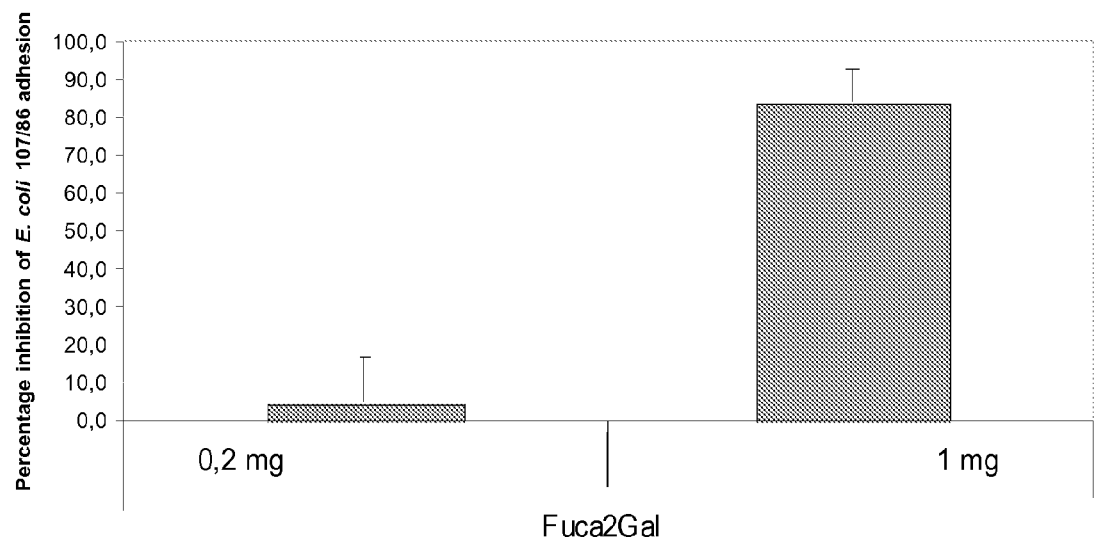

FIG. 9: Effect of preincubation of F18⁺ *E. coli* with blood group H disaccharide. F18⁺ *E. coli* strain 107/86 was incubated with different concentrations (0.2 mg or 1 mg) of blood group H disaccharide (Fucα2Gal) in PBS for 1 h at room temperature. Thereafter, the suspensions were utilized in the in vitro villous adhesion assay

DETAILED DESCRIPTION

Definitions

The glycolipid and carbohydrate nomenclature follows the recommendations by the IUPAC-IUB Commission on Biochemical Nomenclature (CBN for Lipids: *Eur. J. Biochem.* (1998) 257, 293). It is assumed that Gal, Glc, GlcNAc, GalNAc and NeuAc are of the D-configuration, Fuc of the L-configuration, and all monosaccharide units are present in the pyranose form.

With the term "F18 fimbriae" is meant thin, flexible polymeric filaments used by F18⁺ *E. coli* strains to attach to host tissues.

With the term "F18 adhesin" is meant a fimbrial lectin that mediates adhesion to the F18R.

With the term "FedF" is meant the minor adhesive subunit of F18 fimbriae that is expressed by the fed gene cluster.

With the term "receptor binding domain of FedF" is meant a region located at the amino-terminal half of the FedF protein essential for binding and mapped between amino acid 60 and 109.

With the term "the villous adhesion test" is meant the assay as described under Example 1.

With the term "F18 receptor or F18R" is meant a specific carbohydrate receptor on the porcine intestinal epithelium to which F18⁺ *E. coli* can attach.

With the term "F18R positive pig" is meant the F18⁺ *E. coli* susceptible porcine heterozygous FUT1$^{G/A}$ genotype or the F18⁺ *E. coli* susceptible porcine homozygous FUT1$^{G/G}$ genotype.

With the term "F18R negative pig" is meant the F18⁺ *E. coli* resistant porcine genotype FUT1$^{A/A}$.

With the term "compound" is meant a compound of formula (I) or (Ia).

With the term "molecule" is meant an agent identified in the screening methods of the invention.

With the term "labelled" is meant a compound, a molecule or an F18⁺ *E. coli*, F18 fimbriae, F18 adhesin, FedF or the receptor binding domain of FedF labelled with labelling agents.

With the term "carrier" is meant any substance or structure to which a saccharide can attach based on his physical or chemical properties.

With the term "treatment" is meant any treatment of a disease and/or condition in a subject, particularly an animal, and includes: (i) preventing a disease and/or condition from occurring in a subject which may be predisposed to the disease and/or condition but has not yet been diagnosed as having it; (ii) inhibiting the disease and/or condition, i.e., arresting its development; (iii) relieving the disease and/or condition, i.e., causing regression of the disease and/or condition.

Embodiments of the Invention

Uses

The present invention is concerned with use of a compound for binding to F18⁺ *E. coli*, F18 fimbriae, F18 adhesin, FedF or the receptor binding domain of FedF wherein said compound is a compound of formula (I)

$$[X(Fuc\alpha 2)Gal\beta 3(Y)TV]_n\text{-}W \qquad (I)$$

wherein
X is absent, Galα3 or GalNAcα3 and when X is absent, then Y is absent;
Y is absent or Fucα4;
T is absent or ZNAcε3;
and wherein Z is Glc or Gal; and
ε is α or β;
V is absent or a mono- or polysaccharide;
n is 1 or more; and
W is absent or a carrier capable of binding n polysaccharide chains As used herein any monosaccharide written in between regular brackets i.e. ( ) is branched from the main polysaccharide chain and attached to the next in line monosaccharide of said polysaccharide chain as further exemplified below.

As used herein 'polysaccharide' is meant to include any possible combination of two or more monosaccharides giving rise to a chain, whereas with 'polysaccharide chain(s)' in particular is meant [X(Fucα2)Galβ3(Y)TV], wherein X, Y, T and V are defined as for formula (I) above.

For example formula (I) [X(Fucα2)Galβ3(Y)ZNAcε3V]$_n$-W, can schematically be represented by:

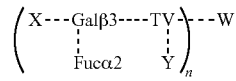

wherein [X(Fucα2)Galβ3(Y)TV] represents the polysaccharide chain attached to the carrier W.

In the context of the present invention, an interesting group of compounds are those compounds of formula (I) or (Ia) wherein when X is absent and Y is absent then Z is Glc.

Another interesting group of compounds are those compounds of formula (I) wherein when X, Y T and V are absent.

Yet another interesting group of compounds are those compounds of formula (I) or (Ia), wherein one polysaccharide chain is attached to said W or wherein W is a multivalent carrier of the polysaccharide chain of the present invention.

When W is a multivalent carrier of the polysaccharide chain it can carry more than one, more than 1000 exemplars of the polysaccharide chain, between 2 and 1000 exemplars of the polysaccharide chain, between 500 to 1000 exemplars of the polysaccharide chain, between 2 and 500 exemplars of the polysaccharide chain, between 2 and 300 exemplars of the polysaccharide chain, between 2 and 100 exemplars of the polysaccharide chain, between 2 and 50 exemplars of the polysaccharide chain, preferably 30; 29; 28; 27; 26; 25; 24; 23; 22; 21; 20; 19; 18; 17; 16; 15; 14; 13; 12; 11; 10; 9; 8; 7; 6; 5; 4; 3 or 2 exemplars of the polysaccharide chain.

W can be but is not limited to proteins, lipids, glycolipids, glycoproteins, glycosphingolipids, ceramides, lectins, antibodies, immunoglobulins, synthetic mimics of the aforementioned carriers, organic molecules, small molecules, chemicals, nanoparticles, beads, gels, etc. . . .

When W is absent, the oligosaccharide sequences according to the present invention are free oligosaccharides, which means that the oligosaccharide sequences are not linked to other mono- or oligosaccharide structures, and present as non-reducing terminal oligosaccharide sequences. When bound to the carrier W, the oligosaccharide sequence is preferably conjugated from the reducing end of the oligosaccharide sequence, though other linkage positions which are tolerated in the aforementioned F18' E. coli binding can also be used. Accordingly, in a particular embodiment, the present invention provides the oligosaccharide sequences according to the present invention as a free oligosaccharide or as a conjugate, in particular a polyvalent conjugate from the reducing end of the oligosaccharide residue.

Another interesting group of compounds within the context of the present invention are those compounds of formula (I) or (Ia), wherein W ceramide and wherein said ceramide is d18:1-16:0, t18:0-16:0, t18:0-h16:0, t18:0-h22:0 or t18:0-h24:0.

In the shorthand nomenclature for fatty acids and bases, the number before the colon refers to the carbon chain length and the number after the colon gives the total number of double bonds in the molecule. Fatty acids with a 2-hydroxy group are denoted by the prefix h before the abbreviation e.g. h16:0. For long chain bases, d denotes dihydroxy and t trihydroxy. Thus d18:1 designates sphingosine (1,3-dihydroxy-2-aminooctadecene) and t18:0 phytosphingosine (1,3,4-trihydroxy-2-aminooctadecene).

Another interesting group of compounds are those compounds of formula (I) or (Ia), wherein X is Galα3 or GalNAcα3; Z is Glc or Gal and Y is absent.

Another interesting group of compounds are those compounds of formula (I) or (Ia) wherein ε is β.

Yet another interesting group of compounds are those compounds of formula (I) or (Ia), wherein Z is Glc.

In a further aspect the present invention provides the use of compounds as described above wherein said compound is a compound of formula (Ia)

[X(Fucα2)Galβ3(Y)ZNAcε3UGalβ4Glcβ1]$_n$-W     (Ia)

wherein
U is absent, Galα4, Galβ3GlcNAcβ3, or (Fucα2)Galβ3GlcNAcβ3

A preferred group of compounds within the context of the present invention for binding to F18⁺ E. coli, F18 fimbriae, F18 adhesin, FedF or the receptor binding domain of FedF are those compounds of formula (I) or (Ia) wherein said compound is selected from the group consisting of

[Fucα2Galβ3]$_n$-W;

[Fucα2Galβ3GlcNAcβ3Galβ4Glcβ1]$_n$-W;

[Galα3(Fucα2)Galβ3GlcNAcβ3Galβ4Glcβ1]$_n$-W;

[GalNAcα3(Fucα2)Galβ3GlcNAcβ3Galβ4Glcβ1]$_n$-W;

[GalNAcα3(Fucα2)Galβ3(Fucα4)
    GlcNAcβ3Galβ4Glcβ1]$_n$-W;

[Galα3(Fucα2)Galβ3(Fucα4)GlcNAcβ3Galβ4Glcβ1]$_n$-W;

[GalNAcα3(Fucα2)
    Galβ3GlcNAcβ3Galβ3GlcNAcβ3Galβ4Glcβ1]$_n$-W;

[GalNAcα3(Fucα2)
    Galβ3GalNAcβ3Galα4Galβ4Glcβ1]$_n$-W; or

[GalNAcα3(Fucα2)Galβ3GalNAcα3(Fucα2)
    Galβ3GlcNAcβ3Galβ4Glcβ1]$_n$-W

Within said embodiment W is either absent or a reducing end conjugate of said oligosaccharide residue; more in particular W is absent and the free polysaccharides are used instead.

Another interesting group of compounds within the context of the present invention for binding to F18⁺ E. coli, F18 fimbriae, F18 adhesin, FedF or the receptor binding domain of FedF are those compounds of formula (I) or (In) wherein said compound is selected from the group consisting of;

Fucα2Galβ3GlcNAcβ3Galβ4Glcβ1Cer;

Galα3(Fucα2)Galβ3GlcNAcβ3Galβ4Glcβ1Cer;

GalNAcα3(Fucα2)Galβ3GlcNAcβ3Galβ4Glcβ1Cer;

GalNAcα3(Fucα2)Galβ3(Fucα4)
    GlcNAcβ3Galβ4Glcβ1Cer;

Galα3(Fucα2)Galβ3(Fucα4)
    GlcNAcβ3Galβ4Glcβ1Cer;

GalNAcα3(Fucα2)
    Galβ3GlcNAcβ3Galβ3GlcNAcβ3Galβ4Glcβ1Cer;

GalNAcα3(Fucα2)
    Galβ3GalNAcβ3Galα4Galβ4Glcβ1Cer;

GalNAcα3(Fucα2)Galβ3GalNAcα3(Fucα2)
    Galβ3GlcNAcβ3Galβ4Glcβ1Cer

In an even more preferred embodiment the compound of formula (I) or (Ia), is

[Galα3(Fucα2)Galβ3GlcNAcβ3Galβ4Glcβ1]$_n$-W; or

[GalNAcα3(Fucα2)Galβ3GlcNAcβ3Galβ4Glcβ1]$_n$-W.

Within said embodiment W is either absent or a reducing end conjugate of said oligosaccharide residue; more in particular W is absent and the free polysaccharides are used instead.

In an even further preferred embodiment the compound of formula (I) or (In), is

Galα3(Fucα2)Galβ3GlcNAcβ3Galβ4Glcβ1Cer; or

GalNAcα3(Fucα2)Galβ3GlcNAcβ3Galβ4Glcβ1Cer.

Compound

Another embodiment of the invention is a compound wherein the compound is

[GalNAcα3(Fucα2)Galβ3GalNAcα3(Fucα2)
    Galβ3GlcNAcβ3Galβ4Glcβ1]$_n$-W wherein W is defined as for formula (I) above.

Screenings Assays

Assays of the present invention can be designed in many formats generally known in the art of screening compounds for biological activity or for binding molecules.

Therefore the present invention is concerned with the use of a compound as described above in a method to identify molecules that affect the binding between F18⁺ E. coli, F18 fimbriae, F18 adhesin, FedF or the receptor binding domain of FedF and said compound.

The described compounds are responsible for one or more biological functions, including one or more disease states, in particular the diseases hereinbefore and hereinafter mentioned. It is therefore desirable to devise screening methods to identify compounds for receptor-based prevention of F18⁺ E. coli infections in pigs The assays of the present invention advantageously exploit the fact that disturbance of the interaction between bindings epitopes of the F18R and F18+ *E. coli,* F18 fimbriae, F18 adhesin, FedF or the receptor binding domain of FedF affect F18+ *E. coli* infections.

Therefore, the present invention includes methods of identifying compounds that interact with the binding between F18+ *E. coli* and the pig epithelium. The assay methods of the present invention differ from those described in the art because they all incorporate at least one step comprising or mimicking the binding interaction between F18+ *E. coli,* F18 fimbriae, F18 adhesins, FedF or the receptor binding domain of FedF, with the F18R.

Knowledge of the carbohydrate receptor for lectins mediating adhesion to the host enables their use as receptor analogues to prevent adherence to the host epithelial surface by competitive inhibition. Bacteria resistant against these receptor analogues may also emerge, but since these agents do not act by killing or arresting the growth of the pathogen, resistant bacteria will be diluted with the sensitive bacteria and will emerge to a much lesser extent, compared to antibiotic-resistant bacteria.

The screening method may simply measure the binding of a candidate molecule to the compound as defined above, or to cells or membranes bearing the compounds as defined above by means of a label directly or indirectly associated with the candidate molecule or with the described compounds.

Thus an embodiment of the present invention is a method to identify molecules that bind to the compounds of formula (I) or (Ia) said method comprising contacting the molecule to be tested with said compound, and determining whether said molecule binds to said compound.

Alternatively, the screening method may involve competition with one of the described compounds.

In the above and the below mentioned method, the molecule to be tested or the described compound used as competitor may be labelled.

Hence another embodiment of the present invention is a method to identify molecules that affect the binding between F18+ *E. coli,* F18 fimbriae, F18 adhesin, FedF or the receptor binding domain of FedF and the compounds of formula (I) or (Ia) comprising:

contacting the molecule to be tested with F18+ *E. coli,* F18 fimbriae, F18 adhesins, FedF or the receptor binding domain of FedF; and said compound, and determining whether said molecule affects the binding of F18+ *E. coli,* F18 fimbriae, F18 adhesin, FedF or the receptor binding domain of FedF with said compound.

Examples of binding assays and competitive binding assays are the in vitro villous adhesion assay and the chromatogram binding assays as described in the examples. Other examples are ELISA's, Immunoassays, RIA's, filter-binding assays, scintillation proximity assays (SPA), Cytostar-T technology, immunoprecipitation assays or the use of a surface plasmon resonance effect exploited by the Biacore instrument.

In the methods described above and below also the F18+ *E. coli,* F18 fimbriae, F18 adhesins, FedF or the receptor binding domain of FedF may be labelled.

Thus, a compound, a molecule or an F18+ *E. coli,* F18 fimbriae, F18 adhesin, FedF or the receptor binding domain of FedF can be labelled with labelling agents, such as radioisotopes, amino acids, enzymes, fluorescent substances, luminous substances, photoaffinitive substances etc. Examples of the radioisotopes include $^{125}I$, $^{131}I$, $^{3}H$ and $^{14}C$. An example of metabolic labelling includes the labelling of *E. coli* strains with $^{35}S$-methionine as described in example 2. Enzymes are usually made detectable by conjugation of an appropriate substrate which, in turn catalyses a detectable reaction. Examples thereof include, but are not limited to beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase.

Molecules may be identified from a variety of sources, for example, cells, cell-free preparations, chemical libraries, and natural product mixtures. Such antagonists so-identified may be natural or modified molecules, ligands, enzymes, etc., as the case may be, of the receptor polypeptide; or may be structural or functional mimetics thereof.

Thus the molecule to be tested may be a lectin, an antibody, a protein, a glycoprotein, a glycolipid, a glycosphingolipid, a small molecule or a synthetic mimic of a compound as described above. Receptor analogs inhibit adhesion of the bacteria via competitive inhibition. Antibodies or lectins will block the carbohydrate receptor Hence the identified molecule can be a F18R receptor analogue or a molecule that blocks the F18R receptor.

In the methods of the present invention the compound, the molecule, the F18+ *E. coli,* F18 fimbriae, F18 adhesins, FedF or the receptor binding domain of FedF can be present on a solid support, a membrane, a cell or a tissue. Examples of solid supports are chromatography plates, ELISA plates, beads such as but not limited to SPA beads or magnetic beads, nanopartikels, filters such as but not limited to nitrocellulose filters or polyvinyldifluoride filters.

Once a molecule has been designed or selected by the above methods, the affinity with which that compound may bind or associate with F18+ *E. coli,* F18 fimbriae, F18 adhesins, FedF, the receptor binding domain of FedF, the defined compounds or a F18R may be tested and optimized by computational evaluation and/or by testing biological activity.

Molecules may interact with F18+ *E. coli,* F18 fimbriae, F18 adhesin, FedF, the receptor binding domain of FedF, the described compounds or a F18R in more than one conformation that is similar in overall binding energy. In those cases, the deformation energy of binding is taken to be the difference between the energy of the free compound and the average energy of the conformations observed when the compound binds.

A molecule designed or selected as binding or associating with F18+ *E. coli,* F18 fimbriae, F18 adhesin, FedF, the receptor binding domain of FedF, the defined compounds or a F18R may be further computationally optimized so that in its bound state it would preferably lack repulsive electrostatic interaction with the binding domains. Such non-complementary (e.g., electrostatic) interactions include repulsive charge-charge, dipole-dipole and charge-dipole interactions. Specifically, the sum of all electrostatic interactions between the inhibitor and a proteasome binding domain or a protein binding domain when the inhibitor is bound, preferably make a neutral or favourable contribution to the enthalpy of binding. Weak binding compounds will also be designed by these methods so as to determine SAR. See, for example, U.S. Appl. Nos. 60/275,629; 60/331,235; 60/379,617; and, Ser. No. 10/097,249.

Specific computer software is available in the art to evaluate molecule deformation energy and electrostatic interaction. Examples of programs designed for such uses include: Gaussian 92, revision C (M. J. Frisch, Gaussian, Inc., Pittsburgh, Pa., COPYRGT 1992); AMBER, version 4.0 (P. A. Kollman, University of California at San Francisco, COPY- RGT 1994); QUANTA/CHARMM (Molecular Simulations, Inc., Burlington, Mass. COPYRGT 1994); and Insight II/Discover (Biosysm Technologies Inc., San Diego, Calif. COPYRGT 1994). Other hardware systems and software packages will be known to those skilled in the art.

Once a molecule that associates with $F18^+$ E. coli, F18 fimbriae, F18 adhesin, FedF, the receptor binding domain of FedF, the defined compounds or a F18R has been optimally selected or designed, as described above, substitutions may then be made in some of its atoms or side groups in order to improve or modify its binding properties. Generally, initial substitutions are conservative, i.e., the replacement group will have approximately the same size, shape, hydrophobicity and charge as the original group. It should, of course, be understood that components known in the art to alter conformation may be avoided. Such substituted chemical molecules may then be analysed for efficiency of fit by the same computer methods described in detail, above.

The compound, molecules and methods as described above and the pharmaceutical compositions, food or drink additive or pig feed described below can also be used to differentiate between F18R positive and negative pigs.

Therefore biological samples of the F18R positive and negative pigs are required. Biological samples can be defined as body tissue or body fluids. Examples of body fluids are cerebrospinal fluid, blood, plasma, serum, urine, sputum, saliva and the like. An example of a body tissue is the intestinal villous material as described in example 1.

Therapeutic Use

In general the defined compounds and molecules may be employed for therapeutic and prophylactic purposes for such diseases as hereinbefore and hereinafter mentioned.

Therefore, the present invention relates to the compounds of formula (I) or (Ia) for use as a medicine.

Thus the present invention relates to the use of compounds of formula (I) or (Ia) or of the selected molecules for the manufacture of a medicament for the treatment of $F18^+$ E. coli infections in pigs in particular in the treatment of post weaning diarrhea and edema disease in pigs. The invention also relates to a compound of formula (I) or (Ia) for use in the treatment of $F18^+$ E. coli infections in pigs in particular in the treatment of post weaning diarrhea and edema disease in pigs.

The present invention further relates to a molecule identified in an assay according to the invention, wherein said molecule is capable of binding to $F18^+$ E. coli, F18 fimbriae, F18 adhesins, FedF or the receptor binding domain of FedF, the above described compounds or an F18R. It further relates to the use of said molecules as a medicine and for use in the treatment of $F18^+$ E. coli infections in pigs.

Thus, in a further aspect, the present invention provides a method for preventing, treating or ameliorating a medical condition related to $F18^+$ E. coli infections which comprises administering to a mammalian subject a therapeutically effective amount of compound or a molecule as described above optionally in combination with a pharmaceutically acceptable carrier, in an amount effective to modulate $F18^+E.$ coli infections. Such pharmaceutically acceptable carriers include, but are not limited to, saline, buffered saline, dextrose, water, glycerol, ethanol, and combinations thereof. Compounds and molecules of the present invention may be employed alone or in conjunction with other compounds, such as therapeutic compounds.

Thus the invention relates to pharmaceutical composition comprising pharmaceutically acceptable carriers and as an active ingredient a therapeutically effective amount of a compound of formula (I) or (Ia) and to a process of preparing a pharmaceutical composition as described above wherein the pharmaceutically acceptable carriers and a compound of formula (I) or (Ia) are intimately mixed.

The compound, molecule or composition will be adapted to the route of administration, for instance an oral route. Administration of these compounds and molecules may be in the form of pills, tablets, capsules, powders, solutions, suspensions, pastes, gels, food additives, drink additives, foods and the like.

The compound, molecule, composition or formulation to be administered will, in any event, contain a quantity of the active compound(s) in an amount effective to alleviate the symptoms of the subject being treated.

The exact dosage and frequency of administration of the present compounds and molecules depends on the particular compound or molecule used, the particular condition being treated, the severity of the condition being treated, the age, weight, gender, diet, time of administration and general physical condition of the particular subject, the mode of administration as well as other medication the subject may be taking, as is well known to those skilled in the art. Furthermore, it is evident that the effective daily amount may be lowered or increased depending on the response of the treated subject and/or depending on the evaluation of the physician prescribing the compounds or molecules of the instant invention.

Dosage forms or compositions containing active ingredient in the range of 0.25 to 95% may be prepared. Depending on the mode of administration, the pharmaceutical composition will preferably comprise from 0.05 to 99% by weight, more preferably from 0.1 to 70% by weight of the active ingredients, and, from 1 to 99.95% by weight, more preferably from 30 to 99.9 weight % of a pharmaceutically acceptable carrier, all percentages being based on the total composition.

Thus the compound of formula (I) or (Ia) or the molecules as described above can be administered as a food or drink additive.

For oral administration, a pharmaceutically acceptable non-toxic composition is formed by the incorporation of any of the normally employed excipients, such as, for example, pharmaceutical grades of mannitol, lactose, cellulose, cellulose derivatives, sodium crosscarmellose, starch, magnesium stearate, sodium saccharin, talcum, glucose, sucrose, magnesium, carbonate, and the like. Such compositions take the form of solutions, suspensions, tablets, pills, capsules, powders, sustained release formulations and the like. Such compositions may contain 1%-95% active ingredient, more preferably 2-50%, most preferably 5-8% active ingredient.

Solid forms can be suitable for solution or suspension in liquid or as emulsions. Suitable excipients are, for example, water, saline, dextrose, glycerol, ethanol or the like. In addition, if desired, the pharmaceutical compositions, food or drink additive to be administered may also contain minor amounts of non-toxic auxiliary substances such as wetting or emulsifying agents, pH buffering agents and the like, such as for example, sodium acetate, sorbitan monolaurate, triethanolamine oleate, triethanolamine sodium acetate, etc.

The percentage of active compound contained in solutions or suspensions is highly dependent on the specific nature thereof, as well as the activity of the compound and the needs of the subject. However, percentages of active ingredient of 0.1% to 10% in solution are employable, and will be higher if the composition is a solid which will be subsequently diluted to the above percentages. Preferably, the composition will comprise 0.2-2% of the active agent in solution.

A further embodiment of the invention is pig feed supplemented with a compound of formula (I) or (Ia), a molecule, a pharmaceutical composition or a food additive as described above. Suitable pig feed include but is not limited to starter feed, weaning feed or fattening feed.

Packs and Kits

Finally, the invention further relates to packs including pharmaceutical packs and kits comprising one or more containers filled with one or more of the ingredients of the aforementioned compounds, molecules, compositions, food or drink additives and pig feed of the invention or methods of the invention.

This invention provides for an article of manufacture comprising a packaging and a pharmaceutical agent, wherein (a) the pharmaceutical agent is one of the compounds as described above or the pharmaceutical agent is identified using an assay of the present invention, and (b) the packaging comprises a label indicating the use of the agent for treating a subject, in particular as a medicine or for the treatment of F18+ E. coli infections in pigs.

This invention will be better understood by reference to the Experimental Details that follow, but those skilled in the art will readily appreciate that these are only illustrative of the invention as described more fully in the claims that follow thereafter. Additionally, throughout this application, various publications are cited. The disclosure of these publications is hereby incorporated by reference into this application to describe more fully the state of the art to which this invention pertains.

Experimental Part

Example 1

In Vitro Villous Adhesion Assay

The nature of the F18R on porcine small intestinal villous enterocytes was investigated using an in vitro villous adhesion inhibition assay (Cox, E., Houvenaghel, A., 1993. Vet. Microbiol. 34(1), 7-18; Verdonck, F., Cox, E., van Gog, K., Van der Stede, Y., Duchateau, L., Deprez, P., Goddeeris, B. M., 2002. Vaccine 20(23-24), 2995-3004). Briefly, a 20 cm intestinal segment was collected from the mid jejunum of a euthanized pig, rinsed three times with ice cold PBS, and fixed with Krebs-Henseleit buffer (160 mM, pH 7.4) containing 1% (v/v) formaldehyde for 30 min at 4° C. Thereafter, the villi were gently scraped from the mucosae with a glass slide and stored in Krebs-Henseleit buffer at 4° C. Treatment of villi with acetone, methanol, 1% Triton® X-100, 10 mM $NaIO_4$ in 0.2M sodium acetate, pH 4.5, or 0.2M sodium acetate, pH 4.5, without $NaIO_4$, respectively, was performed at room temperature on a rotating wheel in a volume of 500 µl during 1 h. Next, the villi were washed 6 times with Krebs-Henseleit buffer followed by addition of $4 \times 10^8$ bacteria of the F18 positive reference E. coli strain (107/86), or the F4ac-expressing E. coli strain GIS 26, to an average of 50 villi in a total volume of 500 µl PBS, supplemented with 1% (w/v) D-mannose in order to prevent adhesion mediated by type 1 pili. These mixtures were incubated at room temperature for 1 h while being gently shaken. Villi were examined by phase-contrast microscopy at a magnification of 600, and the number of bacteria adhering along 50 µm brush border was quantitatively evaluated by counting the number of adhering bacteria at 20 randomly selected places, after which the mean bacterial adhesion was calculated.

Example 2

Bacterial Strains, Culture and Labelling

The verotoxigenic F18 positive E. coli reference strain 107/86 (serotype O139:K12:H1, F18ab+, SLT-IIv+) (Bertschinger H U, Bachmann M, Mettler C, Pospischil A, Schraner E M, Stamm M, Sydler T, Wild P, 1990. Vet Microbiol. 25(2-3):267-81), and the enterotoxigenic F4ac positive E. coli reference strain GIS 26 (serotype O149:K91:F4ac, LT+, STa+, STb+), were cultured on BHI agar plates (Oxoid, Basingstoke, Hampshire, England) at 37° C. for 18 h. Subsequently, the bacteria were harvested by centrifugation and resuspended in phosphate-buffered saline (PBS, pH 7.3). The concentration of bacteria in the suspension was determined by measuring the optical density at 660 nm (OD660). An OD of 1 equals $10^9$ bacteria per ml, as determined by counting colony forming units.

Recombinant E. coli strains expressing whole F18 fimbriae (HB101(pIH120), or F18 fimbriae with deletion of the FedF adhesive subunit (HB101(pIH126)) (Imberechts et al., 1992; 1996), were grown on Iso Sensitest agar plates (Oxoid, Basingstoke, Hampshire, England) supplemented with ampicillin (100 µg/ml) at 37° C. over night. For metabolic labeling, the culture plates were supplemented with 10 µl $^{35}$S-methionine (400 µCi; Amersham Pharmacia Biotech). Bacteria were harvested, washed three times in PBS, and resuspended in PBS containing 2% (w/v) bovine serum albumin, 0.1% (w/v) $NaN_3$ and 0.1% (w/v) Tween 20 (BSA/PBS/TWEEN) to a bacterial density of $1 \times 10^8$ colony forming units/ml. The specific activity of bacterial suspensions was approximately 1 cpm per 100 bacteria.

Example 3

Reference Glycosphingolipids

Total acid and non-acid glycosphingolipid fractions were prepared as described by Karlsson (Karlsson K-A, 1987. Meth. Enzymol. 138:212-220). Individual glycosphingolipids were obtained by repeated chromatography on silicic acid columns and by HPLC, and identified by mass spectrometry (Samuelsson et al., 1990) and proton NMR spectroscopy (Koerner, T. A. W. Jr., J. H. Prestegard, P. C. Demou, and R. K. Yu. 1983. Biochemistry 22:2676-2687).

Example 4

Thin-Layer Chromatography

Aluminium- or glass-backed silica gel 60 high performance thin-layer chromatography plates (Merck, Darmstadt, Germany) were used for thin-layer chromatography, and eluted with chloroform/methanol/water (60:35:8, by volume) as solvent system. The different glycosphingolipids were applied to the plates in quantities of 0.002-4 µg of pure glycosphingolipids and 40 µg of glycosphingolipid mixtures. Chemical detection was done with anisaldehyde (Waldi D, 1962. Sprühreagentien für die dünnschicht-chromatographie, p. 496-515. In Stahl, E. (ed.), Dünnschicht-Chromatographie. Springer-Verlag, Berlin).

Example 5

Chromatogram Binding Assays

Example 5a

Binding of radiolabelled bacteria to glycosphingolipids on thin-layer chromatograms was done as described previously (Hansson G C, Karlsson K-A, Larson G, Strömberg N, Thurin J, 1985. Anal. Biochem. 146:158-163). Dried chromatograms were dipped in diethylether/n-hexane (1:5 v/v) containing 0.5% (w/v) polyisobutylmethacrylate for 1 min, dried, and then blocked with BSA/PBS/TWEEN for 2 h at room temperature. Thereafter, the plates were incubated with $^{35}$S-labeled bacteria (1-5×10$^6$ cpm/ml) diluted in BSA/PBS/TWEEN for another 2 h at room temperature. After washing six times with PBS, and drying, the thin-layer plates were autoradiographed for 12 h using XAR-5 x-ray films (Eastman Kodak, Rochester, N.Y.).

Example 5b

Chromatogram binding assays with monoclonal antibodies directed against the blood group A determinant (DakoCytomation Norden A/S, Glostrup, Denmark) were done as described (Hansson G C, Karlsson K-A, Larson G, McKibbin J M, Blaszczyk M, Herlyn M, Steplewski Z, Koprowski H, 1983. J. Biol. Chem. 258:4091-4097), using $^{125}$I-labeled antimouse antibodies for detection.

Example 6

Isolation of F18-Fimbriated *E. coli* Binding Glycosphingolipids from Porcine Small Intestinal Epithelium Non-acid glycosphingolipids were isolated from epithelial scrapings from porcine small intestines by the method described by Karlsson (Karlsson K-A, 1987. Meth. Enzymol. 138:212-220). Briefly, the epithelial scrapings were lyophilized, and then extracted in two steps in a Soxhlet apparatus with chloroform and methanol (2:1 and 1:9, by volume, respectively). The material obtained was subjected to mild alkaline hydrolysis and dialysis, followed by separation on a silicic acid column. Acid and non-acid glycosphingolipid fractions were obtained by chromatography on a DEAE-cellulose column. In order to separate the non-acid glycolipids from alkali-stable phospholipids, this fraction was acetylated and separated on a second silicic acid column, followed by deacetylation and dialysis. Final purifications were done by chromatographies on DEAE-cellulose and silicic acid columns. The total non-acid glycosphingolipid fractions obtained were thereafter separated, as described below. Throughout the separation procedures aliquots of the fractions obtained were analysed by thin-layer chromatography, and fractions that were coloured green by anisaldehyde were tested for binding of F18-fimbriated *E. coli* using the chromatogram binding assay.

Example 6a

Blood Group O Pig Intestinal Epithelium

A total non-acid glycosphingolipid fraction (148 mg) from blood group O pig intestinal epithelium was first separated on a silicic acid column eluted with increasing volumes of methanol in chloroform. Thereby, an F18-fimbriated *E. coli* binding fraction containing tetraglycosylceramides and more slow-migrating compounds (22 mg) was obtained. This fraction was further separated on an Iatrobeads (Iatrobeads 6RS-8060; Iatron Laboratories, Tokyo) column (10 g), first eluted with chloroform/methanol/water 60:35:8 (by volume), 10×5 ml, followed by chloroform/methanol/water 40:40:12 (by volume), 2×10 ml. The F18-fimbriated *E. coli* binding compound eluted in fractions 3 and 4, and after pooling of these fractions 6.7 mg was obtained. This material was acetylated, and further separated on an Iatrobeads column (2 g), first eluted with increasing volumes of methanol in chloroform. After deacetylation and dialysis, 6.0 mg of pure F18-fimbriated *E. coli*-binding glycosphingolipid (designated fraction O-I) was obtained.

Example 6b

Blood Group A Pig Intestinal Epithelium

A total non-acid glycosphingolipid fraction (183 mg) from blood group A pig intestinal epithelium was initially separated on a silicic acid column eluted with increasing volumes of methanol in chloroform. Pooling of fractions containing tetraglycosylceramides and more slow-migrating compounds yielded 51.2 mg. This material was further separated by HPLC on a 1.0×25 cm silica column (Kromasil Silica, 10 μm particles; Skandinaviska Genetec, Kungsbacka, Sweden) eluted with a linear gradient of chloroform/methanol/water 70:25:4 to 40:40:12 (by volume) during 180 min and with a flow of 2 ml/min. The fractions obtained were pooled according to mobility on thin-layer chromatograms and F18-fimbriated *E. coli* binding activity. Thereby, six F18-fimbriated *E. coli* binding fractions were obtained, designated fraction A-I (12.6 mg), A-II (3.6 mg), A-III (0.3 mg), A-IV (0.5 mg), A-V (0.2 mg) and A-VI (0.2 mg), respectively.

Example 7

Negative Ion FAB Mass Spectrometry

Negative ion FAB mass spectra were recorded on a JEOL SX-102A mass spectrometer (JEOL, Tokyo, Japan). The ions were produced by 6 keV xenon atom bombardment, using triethanolamine (Fluka, Buchs, Switzerland) as matrix, and an accelerating voltage of −10 kV.

Example 8

Endoglycoceramidase Digestion and LC/MS

Endoglycoceramidase II from *Rhodococcus* spp. (Ito and Yamagata, 1989) (Takara Bio Europe S.A., Gennevilliers, France) was used for hydrolysis of glycosphingolipids. Briefly, 50 μg of F18-fimbriated *E. coli* binding fraction O-I from blood group O porcine intestinal epithelium, H type 1 pentaglycosylceramide from human meconium and H type 2 pentaglycosylceramide from human erythrocytes were resuspended in 100 μl 0.05 M sodium acetate buffer, pH 5.0, containing 120 μg sodium cholate, and sonicated briefly. Thereafter, 1 mU of ceramide glycanase was added and the mixture was incubated at 37° C. for 48 h. The reaction was stopped by addition of chloroform/methanol/water to the final proportions 8:4:3 (by volume). The oligosaccharide-containing upper phase thus obtained was separated from detergent on a Sep-Pak QMA cartridge (Waters, Milford, Mass.). The eluant containing the oligosaccharides was dried under nitrogen and under vacuum.

For LC/MS the glycosphingolipid-derived saccharides were separated on a column (200×0.180 mm) packed in-house with 5 μm porous graphite particles (Hypercarb, Thermo Scientific), and eluted with a linear gradient from 0% B to 45% B in 46 min. (Solvent A 8 mM NH$_4$HCO$_3$ and Solvent B 20% 8 mM NH$_4$HCO$_3$/80% acetonitrile (by volume)). Eluted saccharides were analysed in the negative mode on an LTQ linear ion trap mass spectrometer (Thermo Electron, San José, Calif.), using the Xcalibur software.

Example 9

Proton NMR Spectroscopy $^1$H NMR spectra were acquired on a Varian 600 MHz spectrometer at 30° C. Samples were dissolved in dimethyl sulfoxide/D$_2$O (98:2, by volume) after deuterium exchange.

Example 10

Determination of the F18R Nature

Figure 1:
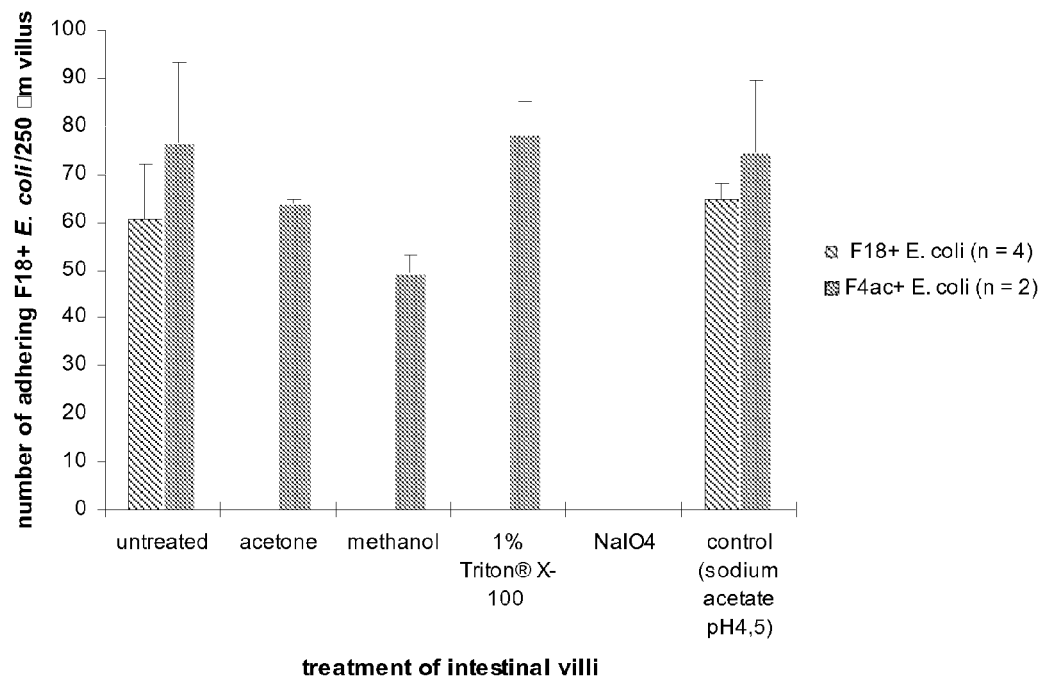
FIG. 1: Effects of treatment with acetone, methanol, 1% Triton® X-100 and NaIO4, on the adherence of F18-fimbriated *E. coli* and F4ac-fimbriated *E. coli* to porcine intestinal villi. The assay was performed as described under "Example 1". The number of pigs investigated is indicated as "n".

To examine the character of the F18R, intestinal villi isolated from four pigs were treated with different agents that affect lipids or carbohydrates on the enterocyte cell membrane. Treatment was followed by assessment of adhesion of F18-fimbriated *E. coli* to the villus epithelium. The adhesion of F18-fimbriated *E. coli* to porcine intestinal villi was completely abolished after treatment with acetone, methanol, 1% Triton® X-100 and NaIO$_4$ (FIG. 1), suggesting that the F18R is a glycolipid. In contrast, the adhesion of the control F4ac-fimbriated *E. coli* strain, having a glycoprotein receptor, was only abolished by incubation with NaIO$_4$, whereas treatment with acetone, methanol and 1% Triton® X-100 had no or only little effect.

Example 11

Screening for F18 Carbohydrate Recognition by Binding to Mixtures of Glycosphingolipids The suggested glycolipid binding of F18-fimbriated *E. coli* was investigated by binding to glycosphingolipids separated on thin-layer plates. The first screening for F18-fimbriated *E. coli* carbohydrate binding activity was done by using mixtures of glycosphingolipids from various sources, in order to expose the bacteria to a large number of potentially binding-active carbohydrate structures. Thereby, binding of the F18-expressing *E. coli* strain HB101(pIH120) to slow-migrating minor non-acid glycosphingolipids from black-and-white rat intestine was obtained (data not shown). Notably, these compounds were not recognized by the *E. coli* strain HB101 (pIH126), having a deletion of the FedF adhesin.

A characteristic feature of black-and-white rat intestine is the presence of glycosphingolipids with blood group A determinants on type 1 (Galβ3GlcNAc) core chains, while in white rat intestine blood group A-terminated glycosphingolipids are absent. When binding of the F18-positive strain HB101 (pIH120) to non-acid glycosphingolipids from white rat intestine was examined, no binding of the bacteria to this fraction occurred (data not shown), in contrast to the binding of the bacteria to the non-acid glycosphingolipid fraction from black-and-white rat intestine. A further observation was the absence of binding of the F18-fimbriated bacteria to the non-acid glycosphingolipids from human blood group A, B or O erythrocytes, where the predominant glycosphingolipids with blood group A, B and H determinants have type 2 (Galβ4GlcNAc) core chains. Once again, no glycosphingolipid was recognized by the FedF deletion mutant HB101 (pIH126).

In summary, the binding of the F18-fimbriated bacteria to slow-migrating minor non-acid glycosphingolipids from black-and-white rat intestine suggested a specific recognition of blood group determinants on type 1 core chains. Furthermore, the absence of binding of the FedF deletion mutant to these compounds indicated an involvement of the FedF protein in the interaction.

Example 12

Binding of F18-Fimbriated *E. coli* to Pure Reference Glycosphingolipids

Binding assays using pure reference glycosphingolipids in defined amounts confirmed the suggested binding of F18-fimbriated *E. coli* to blood group determinants on type 1 core chains. The results (data not shown) are together with results of experiments described below, summarized in Table 1. Thus, the F18-expressing *E. coli* bound to all glycosphingolipids with blood group A, B, or H determinants on type 1 core chains, as the H type 1 pentaglycosylceramide (Fucα2Galβ3GlcNAcβ3Galβ4Glcβ1Cer), the B type 1 hexaglycosylceramide (Galα3(Fucα2)Galβ3GlcNAcβ3Galβ4Glcβ1Cer), the A type 1 hexaglycosylceramide (GalNAcα3(Fucα2)Galβ3GlcNAcβ3Galβ4Glcβ1Cer), the A type 1 heptaglycosylceramide (GalNAcα3(Fucα2)Galβ3(Fucα4)GlcNAcβ3Galβ4Glcβ1Cer) and the B type 1 heptaglycosylceramide (Galα3(Fucα2)Galβ3(Fucα4)GlcNAcβ3Galβ4Glcβ1Cer). In contrast, no type 2 core counterparts of these compounds were recognized by the F18-fimbriated bacteria, as the H type 2 pentaglycosylceramide (Fucα2Galβ4GlcNAcβ3Galβ4Glcβ1Cer), the B type 2 hexaglycosylceramide (Galα3(Fucα2)Galβ4GlcNAcβ3Galβ4Glcβ1Cer), the A type 2 hexaglycosylceramide (GalNAcα3(Fucα2)Galβ4GlcNAcβ3Galβ4Glcβ1Cer), or the A type 2 heptaglycosylceramide (GalNAcα3(Fucα2)Galβ4(Fucα4)GlcNAcβ3Galβ4Glcβ1Cer).

Notably, none of the glycosphingolipids with blood group A, B, or H determinants on type 1 core chains, recognized by the F18-fimbriated bacteria, were bound by the FedF deletion mutant strain HB101(pIH126) (Table 1), demonstrating that the FedF protein is the structural element responsible for binding to the blood group A, B or H type 1-carrying glycosphingolipids.

In addition to these compounds with terminal blood group A/B/H determinants a number of other pure glycosphingolipids were examined for F18-fimbriated *E. coli* binding activity using the chromatogram binding assay, but no further binding-active glycosphingolipids were detected (Table 1).

Comparisons of the relative binding affinity of the F18-fimbriated *E. coli* for the various binding-active glycosphingolipids were done using dilutions of glycosphingolipids on thin-layer chromatograms. The detection limit for the H type 1 pentaglycosylceramide was 2 µg, while the detection limit for the A type 1 hexaglycosylceramide and the B type 1 hexaglycosylceramide were approximately 0.08 µg (data not shown).

Since lactotetraosylceramide (Galβ3GlcNAcβ3Galβ4Glcβ1Cer; No. 20 in Table 1), having an unsubstituted type 1 core chain, was devoid of FedF-mediated binding activity, the terminal α2-linked fucose of the H type 1 pentaglycosylceramide (Fucα2Galβ3GlcNAcβ3Galβ4Glcβ1Cer) was necessary for binding to occur. Of interest in this context is the absence of binding of the F18-fimbriated bacteria to fucosyl-gangliotetraosylceramide (Fucα2Galβ3GalNAcβ4Galβ4Glcβ1Cer; No. 11 in Table 1), demonstrating that the internal N-acetylglucosamine is also mandatory for the binding process. Furthermore, the higher affinity for the B type 1 hexaglycosylceramide (Galα3(Fucα2)Galβ3GlcNAcβ3Galβ4Glcβ1Cer), and the A type 1 hexaglycosylceramide (GalNAcα3(Fucα2)Galβ3GlcNAcβ3Galβ4Glcβ1Cer), demonstrated that the terminal α3-linked galactose/N-acetylgalactosamine of these compounds contributed substantially to the interaction.

The comparison of the binding of F18-positive bacteria to the A type 1 hexaglycosylceramide (GalNAcα3(Fucα2)Galβ3GlcNAcβ3Galβ4Glcβ1Cer) and the A type 1 heptaglycosylceramide (GalNAcα3(Fucα2)Galβ3(Fucα4)GlcNAcβ3Galβ4Glcβ1Cer) revealed that the detection limit for the A type 1 hexaglycosylceramide was approximately 0.08 μg and for the A type 1 heptaglycosylceramide 0.8 μg, demonstrating that substitution of the N-acetylglucosamine with an α-fucose in 4-position constitutes a relative hindrance for binding of the FedF protein. This suggestion is corroborated by the fact that the Le$^b$ hexaglycosylceramide (Fucα2Galβ3(Fucα4)GlcNAcβ3Galβ4Glcβ1Cer; No. 22 in Table 1) is not recognized by the F18-expressing E. coli, although it has the Fucα2Galβ3GlcNAc sequence of the binding active H type 1 pentaglycosylceramide.

Thus, a minimal binding epitope of the FedF adhesin of F18 fimbriae is the linear Fucα2Galβ3GlcNAc sequence, and an optimal binding epitope is created by the addition of the α3-linked galactose or N-acetylgalactosamine of the Galα3(Fucα2)Galβ3GlcNAc and GalNAcα3(Fucα2)Galβ3GlcNAc sequences.

Example 13

Figure 2:
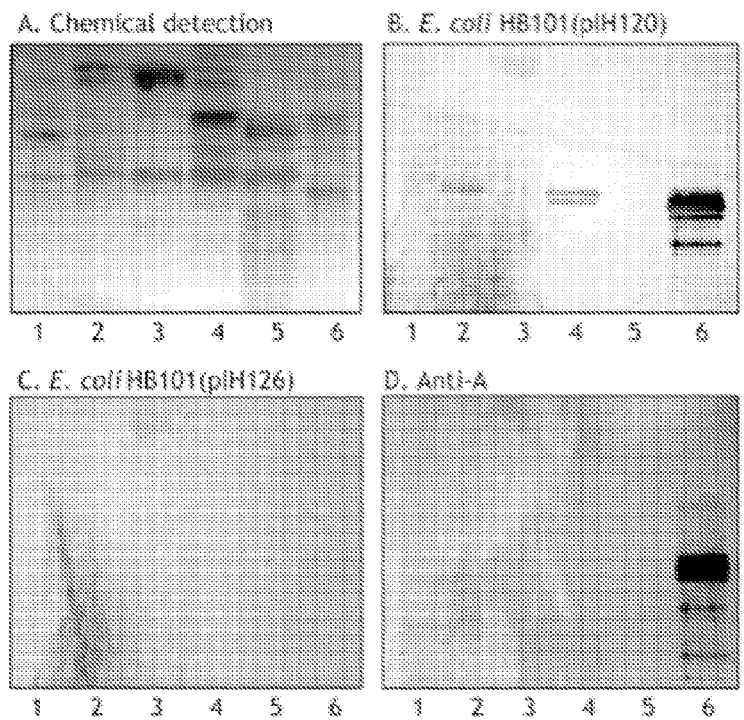
FIG. 2: Binding of recombinant *E. coli* expressing F18 fimbriae (strain HB101(pIH120)), and F18 fimbriae with deletion of the FedF adhesin (strain HB101(pIH126)), to mixtures of glycosphingolipids from porcine small intestinal epithelium on thin-layer chromatograms. The glycosphingolipids were separated on aluminium-backed silica gel plates and visualized with anisaldehyde (A). Duplicate chromatograms were incubated with $^{35}$S-labeled bacteria (B and C), and monoclonal antibodies directed against the blood group A determinant (D), followed by autoradiography for 12 h, as described under "Example 5". The solvent system used was chloroform/methanol/water (60:35:8, by volume). The lanes were: Lane 1, non-acid glycosphingolipids of rabbit small intestine, 40 µg; Lane 2, non-acid glycosphingolipids of 3-day-old piglet small intestinal epithelium, 40 µg; Lane 3, acid glycosphingolipids of 3-day-old piglet small intestinal epithelium, 40 µg; Lane 4, non-acid glycosphingolipids of adult pig small intestinal epithelium (pig No. 1), 40 µg; Lane 5, acid glycosphingolipids of adult pig small intestinal epithelium (pig No. 1), 40 µg; Lane 6, non-acid glycosphingolipids of adult pig small intestinal epithelium (pig No. 2), 40 µg.

Binding of F18-Fimbriated E. coli to Glycosphingolipids from Porcine Small Intestinal Epithelium To assess the potential role of the glycosphingolipid recognition by F18-fimbriated E. coli in target tissue adherence, the binding of the F18-expressing E. coli strain HB101 (pIH120), and FedF deletion mutant strain HB101(pIH126), having a deletion of the FedF adhesin, to acid and non-acid glycosphingolipid fractions from porcine small intestinal epithelium was determined (FIG. 2). No binding to the acid glycosphingolipids (lanes 3 and 5) occurred. However, in the non-acid fractions from a 3-day-old piglet (lane 2), and in the two adult pigs (lanes 4 and 6), binding to some compounds was obtained with the F18-fimbriated strain (FIG. 2B). Notably, these compounds were not recognized by the FedF deletion mutant strain (FIG. 2C).

Two different binding modes were observed for the two non-acid glycosphingolipid fractions from adult pig intestinal epithelium (FIG. 2B, lanes 4 and 6). The fraction in lane 4 (adult pig No. 1) had one binding-active compound migrating in the pentaglycosylceramide region, while in the fraction in lane 6 (adult pig No. 2) binding to a compound migrating in the penta-/hexaosylceramide region was observed, along with binding to a more slow-migrating compound. Several compounds recognized by monoclonal antibodies directed against the blood group A determinant were present in the non-acid fraction from adult pig No. 2 (FIG. 2D, lane 6). The absence of binding of the anti-A monoclonal antibodies to the non-acid glycosphingolipids from 3-day-old piglet, and adult pig No. 1, indicated that these were from blood group O pigs, since blood group B is not expressed in pigs.

Example 14

Isolation and Characterization of the F18-Fimbriated E. coli Binding Glycosphingolipid from Blood Group O Pig Intestinal Epithelium From 148 mg total non-acid glycosphingolipids from the intestinal epithelium of one blood group O pig, 6 mg of pure F18 fimbriae-binding glycosphingolipid (designated fraction O-I) was isolated by a number of chromatographic steps. It should be noted that although all fractions obtained during the isolation procedure were tested for binding of F18-expressing E. coli, no other binding-active glycosphingolipids from this source were detected.

Characterization of the F18-fimbriated E. coli binding glycosphingolipid isolated from blood group O pig intestinal epithelium demonstrated a blood group H type 1 pentaglycosylceramide (Fucα2Galβ3 GlcNAcβ3Galβ4Glcβ1Cer). This conclusion was based on the following three properties:

I) The binding-active compound migrated in the pentaglycosylceramide region on thin-layer chromatograms (FIG. 2B, lane 4).

Figure 3:
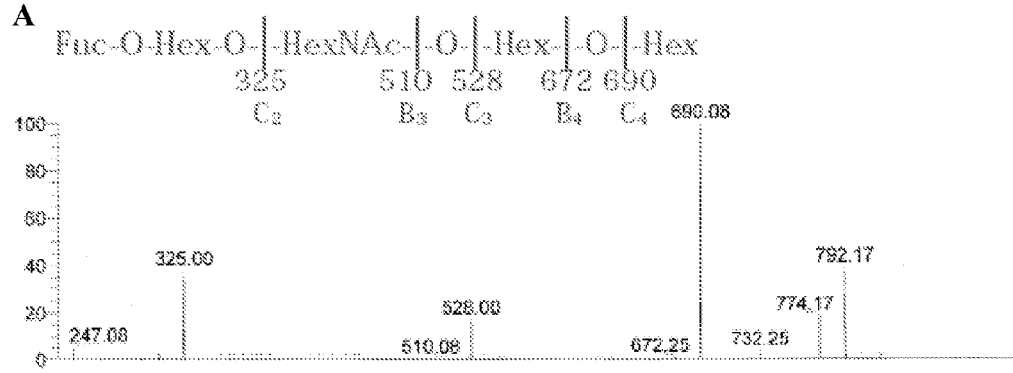
FIG. 3: Nano-LC/MS of the saccharide obtained by digestion with *Rhodococcus* endoglycoceramidase II of the F18 fimbriated *E. coli* binding glycosphingolipid fraction O-I from blood group O pig intestinal epithelium. MS spectra of the [M-H]$^-$ ions at m/z 852 of the saccharides derived from the F18-fimbriated *E. coli*-binding glycosphingolipid from blood group O pig intestinal epithelium (fraction O-I) (A), reference H type 1 pentaglycosylceramide (B), and reference H type 2 pentaglycosylceramide (E).
Figure 3:
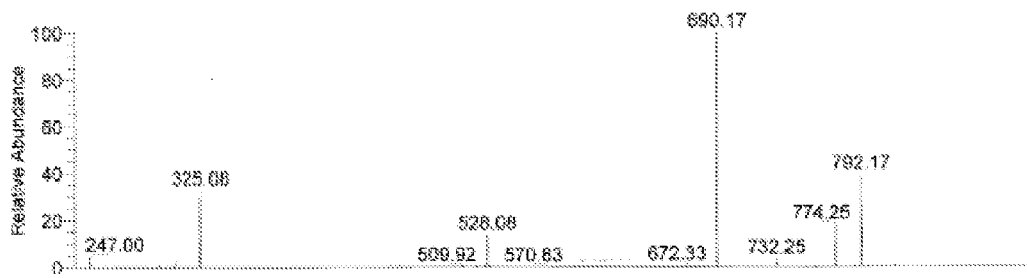
Figure 3:
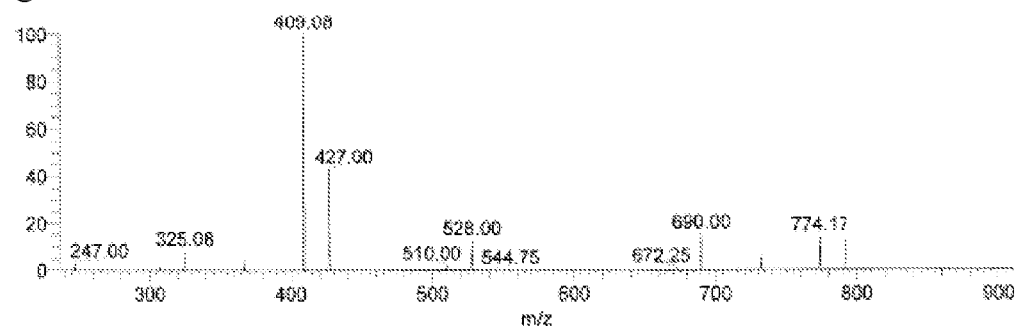

II) In the nano-LC/MS analysis of the saccharides obtained by hydrolysis with Rhodococcus endoglycoceramidase, the retention time and MS spectrum of the saccharide of the porcine pentaglycosylceramide and of reference H type 1 pentaglycosylceramide were almost identical (data not shown). The saccharides were detected as a [M-H]$^-$ ion at m/z 852, and the saccharides from pig intestinal epithelium and from reference H type 1 pentaglycosylceramide both eluted at 22.5-23.3 min, while the saccharide obtained from reference H type 2 pentaglycosylceramide eluted at 24.6-25.1 min. MS of the saccharide released from the pentaglycosylceramide from pig intestinal epithelium (FIG. 3A) and reference H type 1 pentaglycosylceramide (FIG. 3B) resulted in very similar mass spectra with a series of prominent C-type fragment ions ($C_2$ at m/z 325, $C_3$ at m/z 528, and $C_4$ at m/z 690) identifying a pentaglycosylceramide with Fuc-Hex-HexNAc-Hex-Hex sequence. C-type fragment ions at m/z 325, m/z 528, and m/z 690, identifying a Fuc-Hex-HexNAc-Hex-Hex sequence, were also present in the MS spectrum of reference H type 2 pentaglycosylceramide (FIG. 3C). However, this spectrum was dominated by a $^{0,2}A_3$ fragment ion at m/z 427, and a $^{0,2}A_3$-H$_2$O fragment ion at m/z 409, characteristic for GlcNAc substituted at C-4, i.e. type 2 carbohydrate chains (Chai et al., 2001; Robbe et al., 2004).

III) The proton NMR spectrum of the F18-fimbriated E. coli binding pentaglycosylceramide of pig intestine (not shown) revealed five anomeric signals composed of a terminal α and four internal β resonances and the compound was readily identified as the H type 1 pentaglycosylceramide (Fucα2Galβ3GlcNAcβ3Galβ4Glcβ1Cer) through comparison with previously published spectra (Clausen et al., 1985).

Example 15

Isolation of F18-Fimbriated E. coli Binding Glycosphingolipids from Blood Group A Pig Intestinal Epithelium The total non-acid fraction from the intestinal epithelium of one blood group A pig was separated by silica gel chromatography and HPLC, and the subfractions obtained were pooled according to mobility on thin-layer chromatograms and F18-fimbriated E. coli binding activity. Thereby, six F18-fimbriated E. coli binding fractions were obtained, designated fraction A-I (12.6 mg), A-II (3.6 mg), A-III (0.3 mg), A-IV (0.5 mg), A-V (0.2 mg) and A-VI (0.2 mg), respectively (data not shown). Thus, while only one glycosphingolipid with F18-fimbriated E. coli binding activity was obtained from the intestinal epithelium of the blood group O pig, the intestinal epithelium of the blood group A pig had a number of F18-fimbriated *E. coli* binding compounds (Table 2).

Example 16

Characterization of the F18-Fimbriated *E. coli* Binding Glycosphingolipids from Blood Group A Pig Intestinal Epithelium

Example 16a

Fraction A-I

Structural characterization of fraction A-I identified a blood group A6 type 1 hexaglycosylceramide (GalNAcα3(Fucα2)Galβ3 GlcNAcβ3Galβ4Glcβ1Cer). This conclusion is based on the following three observations:
I) On thin-layer chromatograms this F18-fimbriated *E. coli* binding glycosphingolipid migrated in the hexaglycosylceramide region.
II) The negative ion FAB mass spectrum of fraction A-I (not shown) had a series of molecular ions at m/z 1574-1721, identifying a hexaglycosylceramide with one fucose, two HexNAc and three Hex, having a mixed ceramide composition with phytosphingosine and hydroxy 24:0 fatty acid as the predominant species. Fragment ions, derived from the molecular ion at m/z 1721, were found at m/z 1680, 1518, 1372, 1209, 1006, 844 and 682, identifying a HexNAc-(Fuc-)Hex-Hex-NAc-Hex-Hex sequence.
III) Proton NMR spectroscopy (data not shown) showed six anomeric signals at 5.061 ppm (α), 4.913 ppm (α), 4.532 ppm (β), 4.501 ppm (β), 4.259 ppm (β), and 4.208 ppm (β), respectively, and the compound was thus identified as A type hexaglycosylceramide (GalNAcα3(Fucα2)Galβ3GlcNAcβ3Galβ4Glcβ1Cer) through comparison with previously published spectra (Clausen et al., 1985).

Example 16b

Fraction A-II

Figure 4:
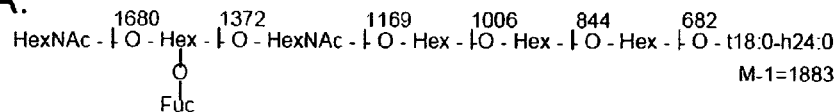
FIG. 4: Characterization of the F18 fimbriated *E. coli* binding heptaglycosylceramide isolated from blood group A pig intestinal epithelium (fraction A-II) by mass spectrometry and proton NMR. (A) Negative ion FAB mass spectrum of fraction A-II. Above the spectrum is an interpretation formula representing the species with t18:0-h24:0 ceramide. The analysis was done as described under "Example 7".
Figure 4:
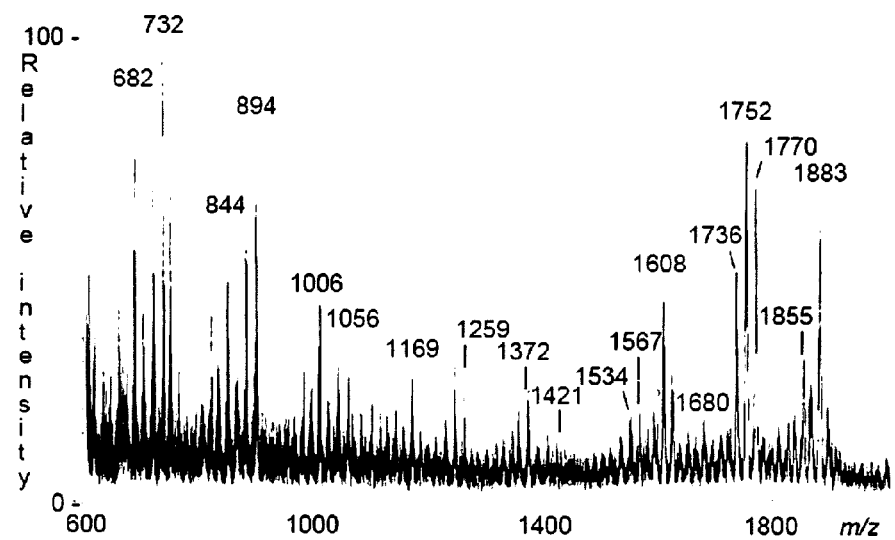
Figure 4:
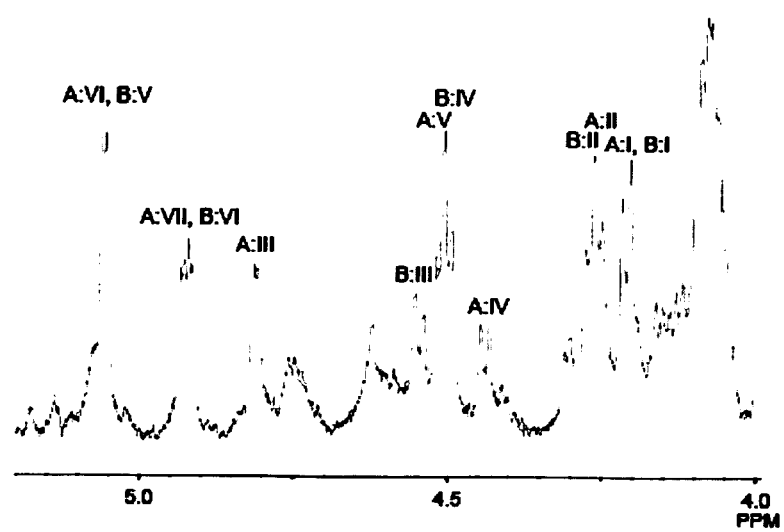

Characterization of F18-fimbriated *E. coli* binding fraction A-II demonstrated a heptaglycosylceramide based on a type 4 chain, i.e. a blood group A type 4 heptaglycosylceramide (GalNAcα3(Fucα2)Galβ3GalNAcβ3Galα4Galβ4Glcβ1Cer) as the major component. This conclusion was based on the following properties:
I) On thin-layer chromatograms the major compound of fraction A-II migrated in the heptaglycosylceramide region. A minor compound migrating in the hexaglycosylceramide region was also observed.
II) The negative ion FAB mass spectrum of fraction A-II (FIG. 4A) had a set of molecular ions at m/z 1736, 1752, 1770, 1855 and 1883 indicating a glycosphingolipid with one Fuc, two HexNAc and four Hex, and d18:1-16:0, t18:0-16:0, t18:0-h16:0, t18:0-h22:0 and t18:0-h24:0 ceramides, respectively. A series of fragment ions, obtained by sequential loss of terminal carbohydrate units from the ion at m/z 1883, were observed at m/z 1680, 1534, 1372, 1169, 1006, 844 and 682, demonstrating a HexNAc-(Fuc-)Hex-HexNAc-Hex-Hex-Hex sequence. Other series of fragment ions supported this proposed carbohydrate sequence, as e.g. the ions derived from the molecular ion at m/z 1770, found at m/z 1567, 1421, 1259, 1056, 894, 732, and 570 (not shown).
III) The anomeric region of the proton NMR spectrum of fraction A-II shown in FIG. 4B revealed the presence of two major compounds (~1:1) of which the first is A6 type 1 as described for the previous fraction. The second compound exhibits seven anomeric signals as follows: 5.056 ppm (α), 4.930 ppm (α), 4.810 ppm (α), 4.510 ppm (β), 4.437 ppm (β), 4.253 ppm (β) and 4.208 ppm (β). This set of signals readily identifies the compound as the A7 type 4 glycosphingolipid (GalNAcα3(Fucα2)Galβ3GalNAcβ3Galα4Galβ4Glcβ1Cer) previously isolated from blood group A1 erythrocytes.

A comparison of the binding of F18-expressing *E. coli* bacteria to the A type 1 hexaglycosylceramide (GalNAcα3(Fucα2)Galβ3GlcNAcβ3Galβ4Glcβ1Cer) and the A type 4 heptaglycosylceramide (GalNAcα3(Fucα2)Galβ3GalNAcβ3Galα4Galβ4Glcβ1Cer) resulted in a detection limit for the A type 1 hexaglycosylceramide of approximately 0.08 μg, while the detection limit for the A type 4 heptaglycosylceramide was approximately 0.8 μg.

Example 16c

Fraction A-III

Structural characterization of F18-fimbriated *E. coli* binding fraction A-III showed that it contained a linear blood group A type 1 octaglycosylceramide (GalNAcα3(Fucα2)Galβ3GlcNAcβ3Galβ3GlcNAcβ3Galβ4Glcβ1Cer) and a novel repetitive A type 1 nonaglycosylceramide (GalNAcα3(Fucα2)Galβ3GalNAcα3(Fucα2)Galβ3GlcNAcβ3Galβ4Glcβ1Cer). This was concluded from the following three observations:
I) Fraction A-III migrated below the heptaglycosylceramide region on thin-layer chromatograms.
II) In the negative ion FAB mass spectrum of fraction A-III (FIG. 5) two sets of molecular ions were observed. The molecular ions at m/z 2204 and 2232 corresponded to a nonaglycosylceramide with two fucoses, three HexNAc and four hexoses, combined with t18:0-h22:0 and t18:0-h24:0 ceramides, respectively. Fragments ions from the molecular ion at m/z 2232, observed at m/z 2086, 2029, 1721, 1517, 1371, 1209, 1006, 844, and 682 (not shown) identified a HexNAc-(Fuc-)Hex-HexNAc-(Fuc-)Hex-HexNAc-Hex-Hex sequence.

The second series of molecular ions at m/z 1958 and 1974 identified an octaglycosylceramide with one fucose, three HexNAc and four hexoses, and with t18:0-16:0 and t18:0-h16:0 ceramides, respectively. Fragments ions derived from the molecular ion at m/z 1958, found at m/z 1755, 1609, 1446, 1243, 1081, 878, 716 (not shown) and 554 (not shown), demonstrated a HexNAc-(Fuc-)Hex-HexNAc-Hex-Hex-NAc-Hex-Hex carbohydrate sequence.
III) The anomeric region of the proton NMR spectrum of fraction A-III (not shown) is complex, consisting of at least four species of which two are dominating. One of the minor contributions is due to the A7 type 4 glycolipid as described above, whereas the two dominating compounds can be ascribed to A8 type 1 (GalNAcα3(Fucα2)Galβ3GlcNAcβ3Galβ3GlcNAcβ3Galβ4Glcβ1Cer) and A9 type 1 (GalNAcα3(Fucα2)Galβ3GalNAcα3(Fucα2)Galβ3GlcNAcβ3Galβ4Glcβ1Cer), of which the former previously has been isolated from rat small intestine. The A8 type 1 structure thus displays the following anomeric signals: 5.066 ppm (Fucα2), 4.917 ppm (GalNAcα3), 4.783 ppm (core GlcNAcβ3), 4.53 ppm (GlcNAcβ3), 4.49 ppm (Galβ3), 4.26 ppm (Galβ4), 4.209 ppm (Glcβ1) and 4.195 ppm (core Galβ3). The latter compound (A9 type 1) has not been described earlier, but differs from the A9 type 3 structure only in that the core Gal at position 4 is 3-linked instead of 4-linked. However, this affects the anomeric region of the NMR spectrum significantly as regards the internal blood group A determinant. The following anomeric signals could be established (the A9 type 3 values measured at 35° C. (Clausen H, Levery S B, Nudelman E, Tsuchiya S, Hakomori S, 1985. Proc Natl Acad Sci USA. 82(4):1199-203.) are given in parenthesis): external GalNAcα3 at 4.950 ppm (4.947), external Fucα2 at 5.055 ppm (5.061), external Galβ3 at 4.657 ppm (4.663), internal GalNAcα3 at 4.933 ppm (4.955), internal Fucα2 at 5.276 ppm (5.329), internal Galβ3 at 4.469 ppm (Galβ4 4.344), core GlcNAcβ3 at 4.50 ppm (4.618), core Galβ4 at 4.26 ppm (4.260) and core Glcβ1 at 4.158 ppm (4.168).

Example 16d

Fractions A-IV-VI

F18-fimbriated *E. coli* binding fractions A-IV-VI migrated below the octaglycosylceramide region on thin-layer chromatograms. The negative ion FAB mass spectra (not shown) of these fractions were very complex. The spectrum of fraction A-IV had two molecular ions at m/z 2407 and 2435, indicating a decaglycosylceramide with two fucoses, four HexNAc and four hexoses, with t18:0-h22:0 and t18:0-h24:0 ceramides, respectively. Fragments ions from the molecular ion at m/z 2435 were observed at m/z 2232, 1924 and 1721, identifying a terminal HexNAc-(Fuc-)Hex-HexNAc sequence.

Negative ion FAB mass spectrometry of fraction A-V demonstrated molecular ions at m/z 2553 and 2581, corresponding to an undecaglycosylceramide with three fucoses, four HexNAc and four hexoses, with t18:0-h22:0 and t18:0-h24:0 ceramides, respectively. A terminal HexNAc-(Fuc-)Hex-HexNAc sequence was suggested by fragment ions from the molecular ion at m/z 2581, found at m/z 2378, 2070 and 1867.

The major compound of fraction A-VI gave rise to molecular ions at m/z 2772 and 2800, which tentatively identified it as a glycosphingolipid with twelve carbohydrate units (two fucoses, five HexNAc and five Hex), combined with t18:0-h22:0 and t18:0-h24:0 ceramides, respectively. Fragments ions from the molecular ion at m/z 2800, observed at m/z 2597, 2289 and 2086, again identified a terminal HexNAc-(Fuc-)Hex-HexNAc sequence.

Example 17

Carbohydrate Inhibition Assay with Blood Group H Type 1 Pentasaccharide and Lacto-N-Tetraose The ability of soluble oligosaccharides (blood group H type 1 pentasaccharide and lacto-N-tetraose) to interfere with the binding of F18-fimbriated *E. coli* to porcine small intestinal cells was evaluated in the in vitro villous adhesion assay.
Materials and Methods
The F18-positive *E. coli* strain 107/86 ($8 \times 10^7$ bacteria) was incubated with different concentrations (10 mg/ml, 1 mg/ml, 100 mg/ml) of blood group H type 1 pentasaccharide (Fucα2Galβ3GlcNAcβ3Galβ4Glc) or lacto-N-tetraose saccharide (Galβ3GlcNAcβ3Galβ4Glc) (Glycoseparations, Moscow, Russia) in a final volume of 100 μl PBS, for 1 h at room temperature, while being gently shaken. The mixtures were then added to the villi, and again incubated for 1 h at room temperature with gentle shaking. Thereafter, the villi were examined by phase-contrast microscopy at a magnification of 600, and the number of bacteria adhering along a 50-nm brush border was quantitatively evaluated by counting the number of adhering bacteria at 20 randomly selected places, after which the mean bacterial adhesion was calculated. Villi of two different F18R-positive pigs were used, and the countings were performed in triplicate. The pigs used were found to be blood group H type 1 and 2 positive, and blood group A type 2 negative, by indirect immunofluorescence using blood group-specific monoclonal antibodies (clone 17-206, GeneTex, Inc., San Antonio, Tex.; clone 92FR-A2, Abcam, Cambridge, UK; clone 29.1 Sigma-Aldrich, St. Louis, Mo.), and FITC-labeled secondary anti-mouse antibody (Sigma-Aldrich).
Results
A strong reduction (87.1%, S.D.=4.5 and 68.5%, S.D.=12.2) of the adherence of F18-positive *E. coli* to porcine intestinal villi of two different pigs was obtained by incubation of the bacteria with 10 mg/ml and 1 mg/ml of the blood group H type 1 pentasaccharide (H5-1, Fucα2Galβ3GlcNAcβ3Galβ4Glc) (FIG. 6), while incubation with 100 mg/ml of the H5-1 saccharide had no visible effect (1.4% inhibition, S.D.=11.14) on the adherence of the bacteria. Incubation with different concentrations (10 mg/ml, 1 mg/ml, 100 mg/ml) of lacto-N-tetraose saccharide (LNT, Galβ3GlcNAcβ3Galβ4Glc) had no effect (5.8% inhibition, S.D.=8.9; 5.8% inhibition, S.D.=6.4 and 4.2% inhibition, S.D.=4.2, respectively) on the adherence of the F18 fimbriated *E. coli*.

Example 18

Carbohydrate Inhibition Assay with Blood Group H Type 1 Pentasaccharide, Blood Group A Type 1 Hexasaccharide, Blood Group B Type 1 Hexasaccharide and Lacto-N-Tetraose Saccharide The ability of soluble oligosaccharides (blood group H type 1 pentasaccharide, blood group A type 1 hexasaccharide, blood group B type 1 hexasaccharide and lacto-N-tetraose) to interfere with the binding of F18-fimbriated *E. coli* to porcine small intestinal cells was evaluated in the in vitro villous adhesion assay.
Materials and Methods
The F18-positive *E. coli* strain 107/86 ($8 \times 10^7$ bacteria) was incubated with 1 mg of blood group H type 1 pentasaccharide (H5-1, Fucα2Galβ3GlcNAcβ3Galβ4Glc), blood group A type 1 hexasaccharide (A6-1, GalNAcα3(Fucα2) Galβ3GlcNAcβ3Galβ4Glc), blood group B type 1 hexasaccharide (B6-1, Galα3(Fucα2)Galβ3GlcNAcβ3Galβ4Glc) or lacto-N-tetraose saccharide (LNT, Galβ3GlcNAcβ3Galβ4Glc) (Elicityl, Grenoble, France) in a final volume of 100 μl PBS, for 1 h at room temperature, while being gently shaken. The mixtures were then added to the villi, and again incubated for 1 h at room temperature with gentle shaking. Thereafter, the villi were examined by phase-contrast microscopy, and adhering bacteria were quantified as described above. Villi of two different F18R-positive pigs were used, and the countings were performed in triplicate. The pigs used were found to be blood group H type 1 and 2 positive, and blood group A type 2 negative, by indirect immunofluorescence using blood group-specific monoclonal antibodies (clone 17-206, GeneTex, Inc., San Antonio, Tex.; clone 92FR-A2, Abcam, Cambridge, UK; clone 29.1 Sigma- Aldrich, St. Louis, Mo.), and FITC-labeled secondary anti-mouse antibody (Sigma-Aldrich).

Results

Pre-incubation of F18-positive *E. coli* with 1 mg of blood group H type 1 pentasaccharide (H5-1, Fucα2Galβ3GlcNAcβ3Galβ4Glc) results in 52.4% inhibition (S.D.=19.9) of F18$^+$ *E. coli* adherence to the porcine intestinal villi of two different pigs (FIG. 7). Pre-incubation of F18$^+$ *E. coli* with 1 mg of blood group A type 1 hexasaccharide (A6-1, GalNAcα3(Fucα2)Galβ3GlcNAcβ3Galβ4Glc) and blood group B type 1 hexasaccharide (B6-1, Galα3(Fucα2)Galβ3GlcNAcβ3Galβ4Glc) lead to 72.9% (S.D.=15.5) and 86.8% (S.D.=11.4) inhibition, respectively. In contrast, incubation with 1 mg lacto-N-tetraose saccharide (LNT) had no effect (2.8% inhibition, S.D.=12.4) on F18$^+$ *E. coli* adherence.

Example 19

Carbohydrate Inhibition Assay with Multivalent Blood Group Sugars

The ability of multivalent blood group sugars to interfere with the binding of F18-fimbriated *E. coli* to porcine small intestinal cells was also evaluated in the in vitro villous adhesion assay.

Materials and Methods

The F18-positive *E. coli* strain 107/86 (8×10$^7$ bacteria) was incubated with different protein concentrations (0.2 μg; 2 μg; 10 μg; 20 μg) of blood group H type 1 pentasaccharide (H5-1, Fucα2Galβ3GlcNAcβ3Galβ4Glc) conjugated to HSA (H5-1/HSA; 25 mole oligosaccharide/mole protein) or incubated with blood group A type 1 hexasaccharide (A6-1, GalNAcα3(Fucα2)Galβ3GlcNAcβ3Galβ4Glc) conjugated to HSA (A6-1/HSA; 9 mole oligosaccharide/mole protein) (IsoSep AB, Tullinge, Sweden) in a final volume of 100 μl PBS, for 1 h at room temperature, while being gently shaken. The mixtures were then added to the villi, and again incubated for 1 h at room temperature with gentle shaking. Thereafter, the villi were examined by phase-contrast microscopy, and adhering bacteria were quantified as described above. Villi of one F18R-positive pig was used, and the countings were performed in duplicate. The pig used was found to be blood group H type 1 and 2 positive, and blood group A type 2 negative, by indirect immunofluorescence using blood group-specific monoclonal antibodies (clone 17-206, GeneTex, Inc., San Antonio, Tex.; clone 92FR-A2, Abcam, Cambridge, UK; clone 29.1 Sigma-Aldrich, St. Louis, Mo.), and FITC-labeled secondary anti-mouse antibody (Sigma-Aldrich).

Results

A strong reduction (71.4%, S.D.=9.2 and 71.1%, S.D.=5.8) of the adherence of F18-positive *E. coli* to porcine intestinal villi was obtained by incubation of the bacteria with 10 μg and 20 μg of the blood group H type 1 pentasaccharide (H5-1, Fucα2Galβ3GlcNAcβ3Galβ4Glc), conjugated to HSA (H5-1/HSA), while incubation with 2 μg H5-1/HSA had only moderate effect (35.8% inhibition, S.D.=11.3) and incubation with 0.2 μg H5-1/HSA had only little effect (18.7% inhibition, S.D.=11.7) on the adherence of F18$^+$ *E. coli* (FIG. 8). Similarly, a strong reduction (67.1%, S.D.=10.8 and 69.1%, S.D.=5.0) of F18$^+$ *E. coli* adherence to porcine intestinal villi was observed after pre-incubation of F18$^+$ *E. coli* with 10 and 20 μg of the blood group A type 1 hexasaccharide (A6-1, GalNAcα3(Fucα2)Galβ3GlcNAcβ3Galβ4Glc), conjugated to HSA (A6-1/HSA). A moderate effect (30.6% inhibition, S.D.=22.2) was observed upon incubation with 2 μg A6-1/HSA, whereas incubation with 0.2 μg A6-1/HSA had only little effect (11.3% inhibition; S.D.=8.6).

No inhibition of F18$^+$ *E. coli* adherence to porcine intestinal villi was obtained when F18$^+$ *E. coli* was pre-incubated with 20 μg HSA.

Example 20

A Method to Identify Molecules that Bind to the Compounds of the Present Invention Materials and Methods To identify molecules such as antibodies or lectins that bind to the compounds of the present invention, a 96-well maxisorb plate was coated with 2.5 μg/ml blood group H type 1 (H5-1, Fucα2Galβ3GlcNAcβ3Galβ4Glc), conjugated to HSA (H5-1/HSA) during 2 hours at 37° C. The plates were blocked overnight at 4° C. with PBS+0.2% Tween® 80. Subsequently, the plates were sequentially incubated with a blood group H type 1-specific monoclonal antibody (clone 17-206, GeneTex, Inc., San Antonio, Tex.) diluted 1/100 in PBS+0.2% Tween® 20+3% BSA and with rabbit anti-mouse-HRP (Dako). Each incubation step of 1 hour was followed by 3 washes with PBS+0.2% Tween® 20. After incubation with the ABTS substrate, the OD$_{405}$ was measured.

Results

An OD$_{405}$ of 1.084 was measured after incubation with the ABTS substrate. This indicates that the blood group H type 1-specific antibody recognizes the blood group H type 1 pentasaccharide, conjugated to HSA. Therefore, we conclude that this method can be used to detect molecules which bind to compounds of the present invention.

Example 21

Carbohydrate Inhibition Assay with Blood Group H Disaccharide (Fucα2Gal)

The ability of the soluble H-disaccharide (Fucα2Gal) to interfere with the binding of F18-fimbriated *E. coli* to porcine small intestinal cells was evaluated in the in vitro villous adhesion assay.

Materials and Methods

The F18-positive *E. coli* strain 107/86 (8×10$^7$ bacteria) was incubated with different concentrations (0.2 mg, 1 mg) of blood group H disaccharide (IsoSep, Sweden) in a final volume of 100 μl PBS, for 1 h at room temperature, while being gently shaken. The mixtures were then added to the villi, and again incubated for 1 h at room temperature with gentle shaking. Thereafter, the villi were examined by phase-contrast microscopy at a magnification of 600, and the number of bacteria adhering along a 50-μm brush border was quantitatively evaluated by counting the number of adhering bacteria at 20 randomly selected places, after which the mean bacterial adhesion was calculated. Villi of one F18R-positive pig were used, and the countings were performed in triplicate.

Results

A strong reduction (83.7%, S.D.=8.8) of the adherence of F18-positive *E. coli* to porcine intestinal villi was obtained by incubation of the bacteria with 1 mg of the blood group H disaccharide (Fucα2Gal) (FIG. 9), while incubation with 0.2 mg of the H disaccharide had no visible effect (5.1% inhibition, S.D.=12.1) on the adherence of the bacteria.

Further to the identification of Fucα2Galβ3GlcNAc as a minimal binding determinant for F18-fimbriated *E Coli* in example 12, we were here able to further pinpoint the minimal binding determinant to Fucα2Gal.

TABLE 1

Binding of $^{35}$S-labelled recombinant F18 fimbriae-expressing *Escherichia coli* (pIH120), and recombinant *E. coli* expressing F18 fimbriae with deletion of the subunit (pIH126), to glycosphingolipids on thin-layer chromatograms

| No. | Trivial name | Structure | pIH120 | pIH126 |
|---|---|---|---|---|
| | | Simple compounds | | |
| 1. | Galactosylceramide | Galβ1Cer | –$^a$ | – |
| 2. | Glucosylceramide | Glcβ1Cer | – | – |
| 3. | Sulfatide | SO$_3$-3Galβ1Cer | – | – |
| 4. | LacCer (d18:1-16:0-24:0)$^b$ | Galβ4Glcβ1Cer | – | – |
| 5. | LacCer (t18:0-h16:0-h24:0) | Galβ4Glcβ1Cer | – | – |
| 6. | Isoglobotri | Galα3Galβ4Glcβ1Cer | – | – |
| 7. | Globotri | Galα4Galβ4Glcβ1Cer | – | – |
| 8. | A-4 | GalNAcα3(Fucα2)Galβ4Glcβ1Cer | – | – |
| | | Ganglioseries | | |
| 9. | GgO3 | GalNAcβ4Galβ4Glcβ1Cer | – | – |
| 10. | GgO4 | Galβ3GalNAcβ4Galβ4Glcβ1Cer | – | – |
| 11. | Fuc-GgO4 | Fucα2Galβ3GalNAcβ4Galβ4Glcβ1Cer | – | – |
| 12. | Sulf-GgO4 | SO$_3$-3Galβ3GalNAcβ4Galβ4Glcβ1Cer | – | – |
| | | Neolactoseries | | |
| 13. | Neolactotetra | Galβ4GlcNAcβ3Galβ4Glcβ1Cer | – | – |
| 14. | H5 type 2 | Fucα2Galβ4GlcNAcβ3Galβ4Glcβ1Cer | – | – |
| 15. | B5 | Galα3Galβ4GlcNAcβ3Galβ4Glcβ1Cer | – | – |
| 16. | B6 type 2 | Galα3(Fucα2)Galβ4GlcNAcβ3Galβ4Glcβ1Cer | – | – |
| 17. | A6 type 2 | GalNAcα3(Fucα2)Galβ4GlcNAcβ3Galβ4Glcβ1Cer | – | – |
| 18. | B7 type 2 | Galα3(Fucα2)Galβ4(Fucα3)GlcNAcβ3Galβ4Glcβ1Cer | – | – |
| 19. | A7 type 2 | GalNAcα3(Fucα2)Galβ4(Fucα3)GlcNAcβ3Galβ4Glcβ1Cer | – | – |
| | | Lactoseries | | |
| 20. | Lactotetra | Galβ3GlcNAcβ3Galβ4Glcβ1Cer | – | – |
| 21. | Le$^a$-5 | Galβ3(Fucα4)GlcNAcβ3Galβ4Glcβ1Cer | – | – |
| 22. | Le$^b$-6 | Fucα2Galβ3(Fucα4)GlcNAcβ3Galβ4Glcβ1Cer | – | – |
| 23. | H5 type 1 | Fucα2Galβ3GlcNAcβ3Galβ4Glcβ1Cer | +++ | – |
| 24. | B6 type 1 | Galα3(Fucα2)Galβ3GlcNAcβ3Galβ4Glcβ1Cer | +++ | – |
| 25. | A6 type 1 | GalNAcα3(Fucα2)Galβ3GlcNAcβ3Galβ4Glcβ1Cer | +++ | – |
| 26. | A7-1 type 1 | GalNAcα3(Fucα2)Galβ3(Fucα4)GlcNAcβ3Galβ4Glcβ1Cer | +++ | – |
| 27. | B7 type 1 | Galα3(Fucα2)Galβ3(Fucα4)GlcNAcβ3Galβ4Glcβ1Cer | +++ | – |
| 28. | A8 type 1 | GalNAcα3(Fucα2)Galβ3GlcNAcβ3Galβ3GlcNAcβ3Galβ4Glcβ1Cer | +++ | – |
| 29. | A9 type 1 | GalNAcα3(Fucα2)Galβ3GalNAcα3(Fucα2)Galβ3GlcNAcβ3Galβ4Glcβ1Cer | +++ | – |
| | | Globoseries | | |
| 30. | Globotetra | GalNAcβ3Galα4Galβ4Glcβ1Cer | – | – |
| 31. | Forssman | GalNAcα3GalNAcβ3Galα4Galβ4Glcβ1Cer | – | – |
| 32. | A7 type 4 | GalNAcα3(Fucα2)Galβ3GalNAcβ3Galα4Galβ4Glcβ1Cer | +++ | – |
| | | Gangliosides | | |
| 33. | NeuGc-GM3 | NeuGcα3Galβ4Glcβ1Cer | – | – |
| 34. | NeuGc-GM1 | Galβ3GalNAcβ4(NeuGcα3)Galβ4Glcβ1Cer | – | – |
| 35. | NeuAc-GM1 | Galβ3GalNAcβ4(NeuAcα3)Galβ4Glcβ1Cer | – | – |
| 36. | NeuAc-GD1b | Galβ3GalNAcβ4(NeuAcα8NeuAcα3)Galβ4Glcβ1Cer | – | – |
| 37. | NeuAcα3SPG | NeuAcα3Galβ4GlcNAcβ3Galβ4Glcβ1Cer | – | – |

$^a$Binding is defined as follows: +++ denotes an intense staining when when 4 μg of the glycosphingolipid was applied on the thin-layer chromatogram, + denotes a staining, while – denotes no binding even at 4 μg.
$^b$In the shorthand nomenclature for fatty acids and bases, the number before the colon refers to the carbon chain length and the number after the colon gives the total number of double bonds in the molecule. Fatty acids with a 2-hydroxy group are denoted by the prefix h before the abbreviation e.g. h16:0. For long chain bases, d denotes dihydroxy and t trihydroxy. Thus d18:1 designates sphingosine (1,3-dihydroxy-2-aminooctadecene) and t18:0 phytosphingosine (1,3,4-trihydroxy-2-aminooctadecene).

TABLE 2

Overview of F18-fimbriated *E. coli* binding glycosphingolipids isolated from a blood group O and A pig

| pig | fraction | amount | identity |
|---|---|---|---|
| blood group O pig | O-I | 6.0 mg | H type 1 pentaglycosylceramide<br>Fuc$_α$2Gal$_β$3GlcNAc$_β$3Gal$_β$4Glc$_β$1Cer |
| blood group A pig | A-I | 12.6 mg | A type 1 hexaglycosylceramide<br>GalNAc$_α$3(Fuc$_α$2)Gal$_β$3GlcNAc$_β$3Gal$_β$4Glc$_β$1Cer |
| | A-II | 3.6 mg | A type 4 heptaglycosylceramide<br>GalNAc$_α$3(Fuc$_α$2)Gal$_β$3GalNAc$_β$3Gal$_α$4Gal$_β$4Glc$_β$1Cer |
| | A-III | 0.3 mg | A type 1 octaglycosylceramide<br>GalNAc$_α$3(Fuc$_α$2)Gal$_β$3GlcNAc$_β$3Gal$_β$3GlcNAc$_β$3Gal$_β$4Glc$_β$1Cer<br>A type 1 nonaglycosylceramide<br>GalNAc$_α$3(Fuc$_α$2)Gal$_β$3GalNAc$_α$3(Fuc$_α$2)Gal$_β$3GlcNAc$_β$3Gal$_β$4Glc$_β$1Cer |

TABLE 2-continued

Overview of F18-fimbriated *E. coli* binding glycosphingolipids isolated from a blood group O and A pig

| pig | fraction | amount | identity |
|---|---|---|---|
| | A-IV | 0.5 mg | decaglycosylceramide<br>two fucoses, four HexNAc and four hexoses |
| | A-V | 0.2 mg | undecaglycosylceramide<br>three fucoses, four HexNAc and four hexoses |
| | A-VI | 0.2 mg | glycosphingolipid with 12 carbohydrate units<br>two fucoses, five HexNAc and five hexoses |

What is claimed is:

1. A method for the treatment or prevention of F18+ *E. coli* infections in pigs comprising: administering to a pig a compound for binding to F18+ *E. coli*, F18 fimbriae, F18 adhesin, FedF or the receptor binding domain of FedF, said compound having the formula (I)

[X(Fucα2)Galβ3(Y)ZNacε3V]$_n$-W    (I)

wherein
X is absent, Galα3 or GalNAcα3 and when X is absent, then Y is absent;
Y is absent or Fucα4;
Z is Glc or Gal;
ε is α or β;
V is absent or a mono- or polysaccharide;
n is 1 or more; and
W is absent or a carrier capable of binding n polysaccharide chains, said carrier selected from the group consisting of a protein, a lipid, a glycolipid, a glycoprotein, a glycosphingolipid, a ceramide, a lectin, an antibody, an immunoglobuline, a synthetic mimic of the aforementioned carrier, an organic molecule, a small molecule, a chemical, a nanoparticle, a bead, or a gel.

2. The method according to claim 1 wherein said pig has post weaning diarrhea or edema disease.

3. The method according to claim 1, wherein V is UGalβ4Glcβ1; and wherein U is absent, Galα4, Galβ3GlcNAcβ3, or (Fucα2)Galβ3GlcNAcβ3.

4. The method according to claim 1, wherein X is Galα3 or GalNAcα3; Z is Glc or Gal and Y is absent.

5. The method according to claim 1, wherein ε is β and Z is Glc.

6. The method according to claim 1, wherein X, Y, and V are absent.

7. The method according to claim 1, wherein said compound is a compound of formula (Ia)

[X(Fucα2)Galβ3(Y)ZNacε3UGalβ4Glcβ1]$_n$-W    (Ia)

wherein
U is absent, Galα4, Galβ3GlcNAcβ3, or (Fucα2)Galβ3GlcNAcβ3.

8. The method according to claim 1, wherein W is absent or ceramide.

9. The method according to claim 1, wherein said compound is selected from the group consisting of:

Fucα2Galβ3GlcNAcβ3Galβ4Glc;

Galα3(Fucα2)Galβ3GlcNAcβ3Galβ4Glc;

GalNAcα3(Fucα2)Galβ3GlcNAcβ3Galβ4Glc;

GalNAcα3(Fucα2)Galβ3(Fucα4)GlcNAcβ3Galβ4Glc;

Galα3(Fucα2)Galβ3(Fucα4)GlcNAcβ3Galβ4Glc;

GalNAcα3(Fucα2)Galβ3GlcNAcβ3Galβ3GlcNAcβ3Galβ4Glc;

GalNAcα3(Fucα2)Galβ3GalNAcβ3Galα4Galβ4Glc; or

GalNAcα3(Fucα2)Galβ3GalNAcα3(Fucα2)Galβ3GlcNAcβ3Galβ4Glc;

and a reducing-end polyvalent conjugate of one or more of these compounds.

10. The method according to claim 1, wherein the compound is administered as a pig feed supplement.

* * * * *